US012667249B2

(12) United States Patent
Watanabe

(10) Patent No.: US 12,667,249 B2
(45) Date of Patent: Jun. 30, 2026

(54) IMAGE PROCESSING APPARATUS, ENDOSCOPE SYSTEM, OPERATION METHOD OF IMAGE PROCESSING APPARATUS, AND NON-TRANSITORY COMPUTER READABLE MEDIUM

(71) Applicant: FUJIFILM Corporation, Tokyo (JP)

(72) Inventor: Hiroki Watanabe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 273 days.

(21) Appl. No.: 18/191,882

(22) Filed: Mar. 29, 2023

(65) Prior Publication Data

US 2023/0237659 A1      Jul. 27, 2023

Related U.S. Application Data

(63) Continuation of application No. PCT/JP2021/035912, filed on Sep. 29, 2021.

(30) Foreign Application Priority Data

Oct. 2, 2020   (JP) ................................ 2020-167816

(51) Int. Cl.
*G06T 7/00*      (2017.01)
*A61B 1/00*      (2006.01)
      (Continued)

(52) U.S. Cl.
CPC ...... *G06T 7/0014* (2013.01); *A61B 1/000095* (2022.02); *A61B 1/0005* (2013.01);
      (Continued)

(58) Field of Classification Search
CPC ........... G06T 7/0014; G06T 5/50; G06T 5/92; G06T 11/00; G06T 2207/10068;
      (Continued)

(56) References Cited

U.S. PATENT DOCUMENTS 12,217,445 B2 *  2/2025  Choi ......................... G06T 7/62
2009/0074268 A1  3/2009  Tanaka et al.
      (Continued)

FOREIGN PATENT DOCUMENTS

CN       110475503       11/2019
EP       3603481       5/2023
      (Continued)

OTHER PUBLICATIONS

"Search Report of Europe Counterpart Application", issued on Feb. 12, 2024, p. 1-p. 8.
      (Continued)

*Primary Examiner* — Matthew C Bella
*Assistant Examiner* — Daniel Joseph Santos
(74) *Attorney, Agent, or Firm* — JCIPRNET

(57) ABSTRACT

The image processing apparatus acquires a plurality of types of candidate images based on an endoscope image, performs control of displaying, on a display, a display image based on at least one type of candidate image, performs a first analysis process on one or the plurality of types of candidate images set in advance, selects at least one type of candidate image from the plurality of types of candidate images as an optimum image based on a first analysis process result obtained through the first analysis process, and obtains a second analysis process result by performing a second analysis process on the optimum image.

16 Claims, 24 Drawing Sheets

(51) Int. Cl.

| | |
|---|---|
| *A61B 1/06* | (2006.01) |
| *G06T 5/50* | (2006.01) |
| *G06T 5/92* | (2024.01) |
| *G06T 11/00* | (2026.01) |
| *G16H 30/40* | (2018.01) |

(52) U.S. Cl.

CPC .............. *A61B 1/0638* (2013.01); *G06T 5/50* (2013.01); *G06T 5/92* (2024.01); *G06T 11/00* (2013.01); *G16H 30/40* (2018.01); *G06T 2207/10068* (2013.01); *G06T 2207/20208* (2013.01); *G06T 2207/30028* (2013.01); *G06T 2207/30096* (2013.01); *G06T 2207/30104* (2013.01); *G06T 2210/41* (2013.01)

(58) Field of Classification Search

CPC . G06T 2207/20208; G06T 2207/30028; G06T 2207/30096; G06T 2207/30104; G06T 2210/41; G06T 2207/30004; G06T 2207/30168; G06T 7/0002; G06T 11/60; A61B 1/000095; A61B 1/0005; A61B 1/0638; A61B 1/045; G16H 30/40; G16H 30/20; G16H 50/20; G16H 50/70

USPC ........................................................ 382/128

See application file for complete search history.

(56) References Cited

U.S. PATENT DOCUMENTS

| | | | |
|---|---|---|---|
| 2019/0073769 A1 | 3/2019 | Watanabe | |
| 2020/0022560 A1* | 1/2020 | Oosake .............. | A61B 1/00009 |
| 2020/0193236 A1* | 6/2020 | Oosake ................ | G06K 9/6262 |

| | | | |
|---|---|---|---|
| 2020/0242764 A1 | 7/2020 | Aoyama | |
| 2021/0113075 A1 | 4/2021 | Ito et al. | |
| 2021/0145248 A1 | 5/2021 | Ito et al. | |
| 2023/0119040 A1 | 4/2023 | Aoyama | |

FOREIGN PATENT DOCUMENTS

| | | |
|---|---|---|
| JP | 2007244518 | 9/2007 |
| JP | 2010172673 | 8/2010 |
| JP | 2018175762 | 11/2018 |
| JP | 2019042157 | 3/2019 |
| JP | 2020065685 | 4/2020 |
| WO | 2019078204 | 4/2019 |
| WO | 2020012563 | 1/2020 |
| WO | 2020012564 | 1/2020 |

OTHER PUBLICATIONS

"International Search Report (Form PCT/ISA/210) of PCT/JP2021/035912", mailed on Dec. 28, 2021, with English translation thereof, pp. 1-5.

"Written Opinion of the International Searching Authority (Form PCT/ISA/237) of PCT/ JP2021/035912", mailed on Dec. 28, 2021, with English translation thereof, pp. 1-6.

"Office Action of Japan Counterpart Application", issued on Mar. 4, 2025, with English translation thereof, p. 1-p. 6.

"Office Action of China Counterpart Application", issued on Jul. 16, 2025, with English translation thereof, p. 1-p. 16.

"The Second Office Action of China Counterpart Application", issued on Dec. 9, 2025, with English translation thereof, p. 1-p. 14.

"Rejection Decision of China Counterpart Application", issued on Mar. 13, 2026, with English translation thereof, p. 1-p. 12.

* cited by examiner

FIG. 6
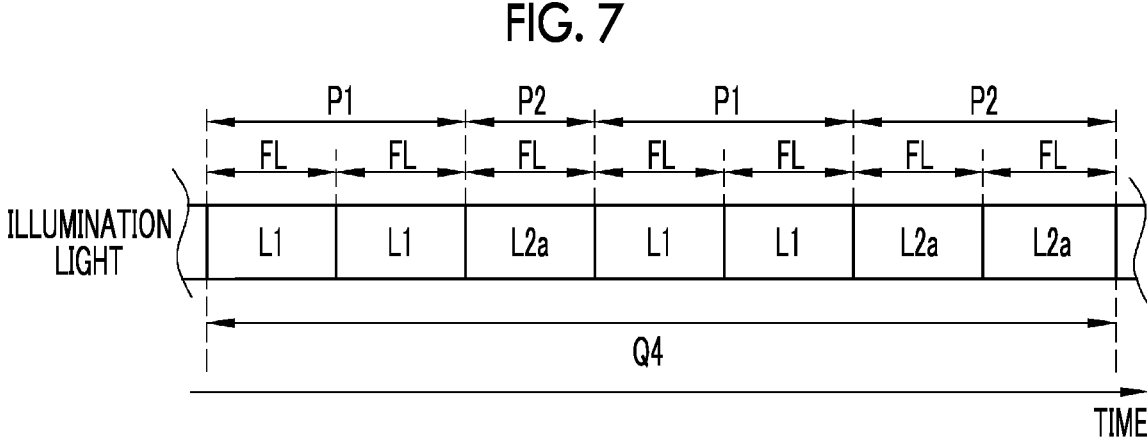
FIG. 7
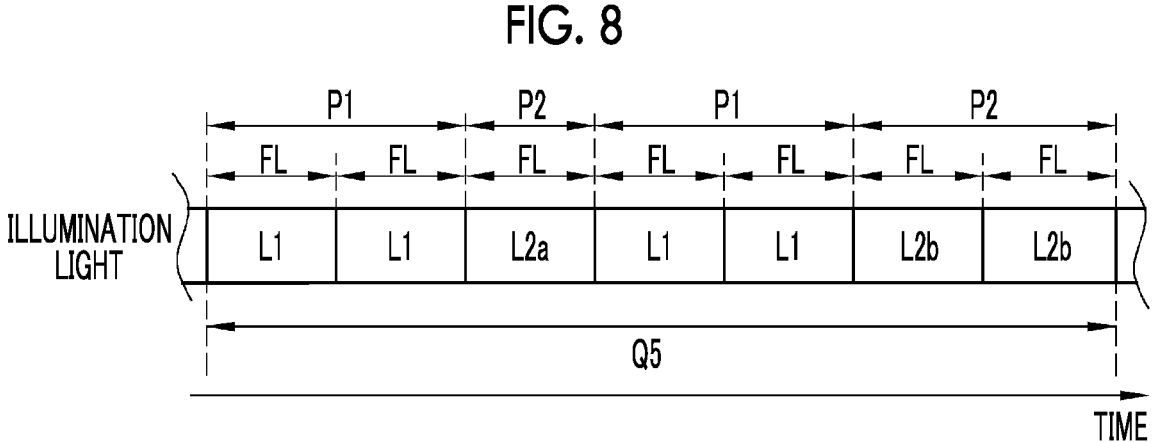
FIG. 8

IMAGE PROCESSING APPARATUS, ENDOSCOPE SYSTEM, OPERATION METHOD OF IMAGE PROCESSING APPARATUS, AND NON-TRANSITORY COMPUTER READABLE MEDIUM

CROSS-REFERENCE TO RELATED APPLICATIONS

This application is a Continuation of PCT International Application No. PCT/JP2021/035912 filed on 29 Sep. 2021, which claims priority under 35 U.S.C § 119(a) to Japanese Patent Application No. 2020-167816 filed on 2 Oct. 2020. The above application is hereby expressly incorporated by reference, in its entirety, into the present application.

BACKGROUND OF THE INVENTION

1. Field of the Invention

The present invention relates to an image processing apparatus, an endoscope system, an operation method of an image processing apparatus, and a program for an image processing apparatus that obtain diagnosis support information.

2. Description of the Related Art

In the medical field, diagnosis using an endoscope system that comprises a light source device, an endoscope, and a processor device is widely performed. A doctor uses various types of endoscope images displayed with colors, structures such as blood vessels, or the like enhanced to diagnose an observation target through an image enhanced endoscope or a method called an image enhanced endoscopy (IEE) in some cases, in addition to displaying an image (hereinafter, referred to as an endoscope image) obtained by imaging the observation target with an endoscope on a display or the like in natural colors.

In addition, computer-aided diagnosis (CAD) technology, in which diagnosis support information including a determination result such as a stage of a disease is generated from a range of a region having a possibility of being a lesion in an observation target and/or a degree of inflammation by analyzing various types of endoscope images through IEE or the like, has been developed. For example, an endoscope system that accurately determines the severity or degree of progression of a disease, such as the stage of ulcerative colitis, using various types of endoscope images obtained through IEE is known (JP2020-65685A). In addition, an endoscope apparatus that obtains diagnosis support information after selecting an image having brightness suitable for CAD is known (WO2020/012564A, corresponding to US2021/145248A1).

SUMMARY OF THE INVENTION

Since various types of endoscope images obtained through IEE or the like are used for diagnosis by a doctor or the like, the endoscope images are colored images that do not give a sense of incongruity in a case of being viewed by humans in some cases. The endoscope images which are obtained through IEE and which have good visibility for humans are not limited to endoscope images from which diagnosis support information is obtained well through image analysis based on CAD or the like in some cases. That is, there can be an endoscope image that has poor visibility for humans but is suitable for image analysis based on CAD or the like. Therefore, there is a possibility in which more accurate diagnosis support information is obtained by performing CAD or the like using a type of endoscope image appropriate for image analysis based on CAD or the like.

In addition, by obtaining detailed diagnosis support information real time during endoscopy using CAD or the like, for example, a doctor can discover a region having a high probability of being a lesion and examine the region in one endoscopy in detail. In this case, this is preferable since it is not necessary to perform endoscopy again, but it is necessary to quickly obtain diagnosis support information during examination. In addition, from a perspective of reducing a burden on an examinee of endoscopy and improving endoscopy efficiency, it is preferable to quickly obtain diagnosis support information while performing CAD or the like.

An object of the present invention is to provide an image processing apparatus, an endoscope system, an operation method of an image processing apparatus, and a non-transitory computer readable medium that can obtain diagnosis support information quickly and accurately.

According to an aspect of the present invention, there is provided an image processing apparatus comprising an image processor. The image processor is configured to acquire a plurality of types of candidate images based on an endoscope image obtained by imaging an observation target using an endoscope, perform control of displaying, on a display, a display image based on at least one type of the candidate image among the plurality of types of candidate images, perform a first analysis process on one or the plurality of types of candidate images set in advance among the plurality of types of candidate images, select at least one type of the candidate image from the plurality of types of candidate images as an optimum image based on a first analysis process result obtained through the first analysis process, and obtain a second analysis process result by performing a second analysis process on the optimum image.

It is preferable that the image processor is configured to perform control of displaying the second analysis process result on the display.

It is preferable that the image processor is configured to perform control of superimposing the second analysis process result on the display image and displaying the superimposed display image.

It is preferable that the first analysis process and the second analysis process are analysis processes having contents different from each other.

It is preferable that the candidate image is generated by performing an enhancement process on the endoscope image and the image processor is configured to distinguish types of the candidate images depending on presence or absence or a type of the enhancement process and to acquire the plurality of types of candidate images.

It is preferable that the enhancement process is a color enhancement process and/or a structure enhancement process.

In addition, according to another aspect of the present invention, there is provided an endoscope system comprising the image processing apparatus and a light source unit that emits illumination light with which the observation target is irradiated.

It is preferable that the image processor is configured to acquire the endoscope image obtained by imaging the observation target illuminated with each of a plurality of types of illumination light emitted by the light source unit, which have optical spectra different from each other, as each of different types of the candidate images from each other.

It is preferable that the light source unit repeatedly emits each of a plurality of types of illumination light, which have optical spectra different from each other, in a light emission period consisting of order set in advance.

It is preferable that the image processor is configured to select at least one optimum image from the plurality of types of candidate images obtained in the one light emission period.

It is preferable that a light source processor configured to emit first illumination light in a first light emission pattern during a first illumination period, emit second illumination light in a second light emission pattern during a second illumination period, and switch between the first illumination light and the second illumination light and an image pick-up sensor that outputs a first endoscope image obtained by imaging an observation target illuminated with the first illumination light and a second endoscope image obtained by imaging the observation target illuminated with the second illumination light are further included and the image processor is configured to acquire the first endoscope image and the second endoscope image as the candidate images.

It is preferable that the image processor is configured to acquire the endoscope image obtained by imaging the observation target illuminated with white illumination light emitted by the light source unit as one type of the candidate image.

It is preferable that the image processor is configured to acquire the endoscope image obtained by imaging the observation target illuminated with illumination light, which is emitted by the light source unit and includes narrowband light in a wavelength range set in advance, as one type of the candidate image.

In addition, according to another aspect of the present invention, there is provided an operation method of an image processing apparatus comprising a candidate image acquisition step of acquiring a plurality of types of candidate images based on an endoscope image obtained by imaging an observation target using an endoscope, a display image control step of performing control of displaying, on a display, a display image based on at least one type of the candidate image among the plurality of types of candidate images, a first analysis processing step of performing a first analysis process on one or the plurality of types of candidate images set in advance among the plurality of types of candidate images, an optimum image selection step of selecting at least one type of the candidate image from the plurality of types of candidate images as an optimum image based on a first analysis process result obtained through the first analysis process, and a second analysis processing step of obtaining a second analysis process result by performing a second analysis process on the optimum image.

In addition, according to still another aspect of the present invention, there is provided a non-transitory computer readable medium for storing a computer-executable program for causing a computer to function as an image processing apparatus, the program causing the computer to execute a candidate image acquisition function of acquiring a plurality of types of candidate images based on an endoscope image obtained by imaging an observation target using an endoscope, a display control function of performing control of displaying, on a display, a display image based on at least one type of the candidate image among the plurality of types of candidate images, a first analysis processing function of performing a first analysis process on one or the plurality of types of candidate images set in advance among the plurality of types of candidate images, an optimum image selection function of selecting at least one type of the candidate image from the plurality of types of candidate images as an optimum image based on a first analysis process result obtained through the first analysis process, and a second analysis processing function of obtaining diagnosis support information by performing a second analysis process on the optimum image.

With the present invention, diagnosis support information can be obtained quickly and accurately.

BRIEF DESCRIPTION OF THE DRAWINGS

FIG. 5 is an explanatory view for describing a first B light emission pattern.

FIG. 6 is an explanatory view for describing a second B light emission pattern.

FIG. 7 is an explanatory view for describing a second C light emission pattern.

FIG. 8 is an explanatory view for describing a second D light emission pattern.

DESCRIPTION OF THE PREFERRED EMBODIMENTS

Figure 1:
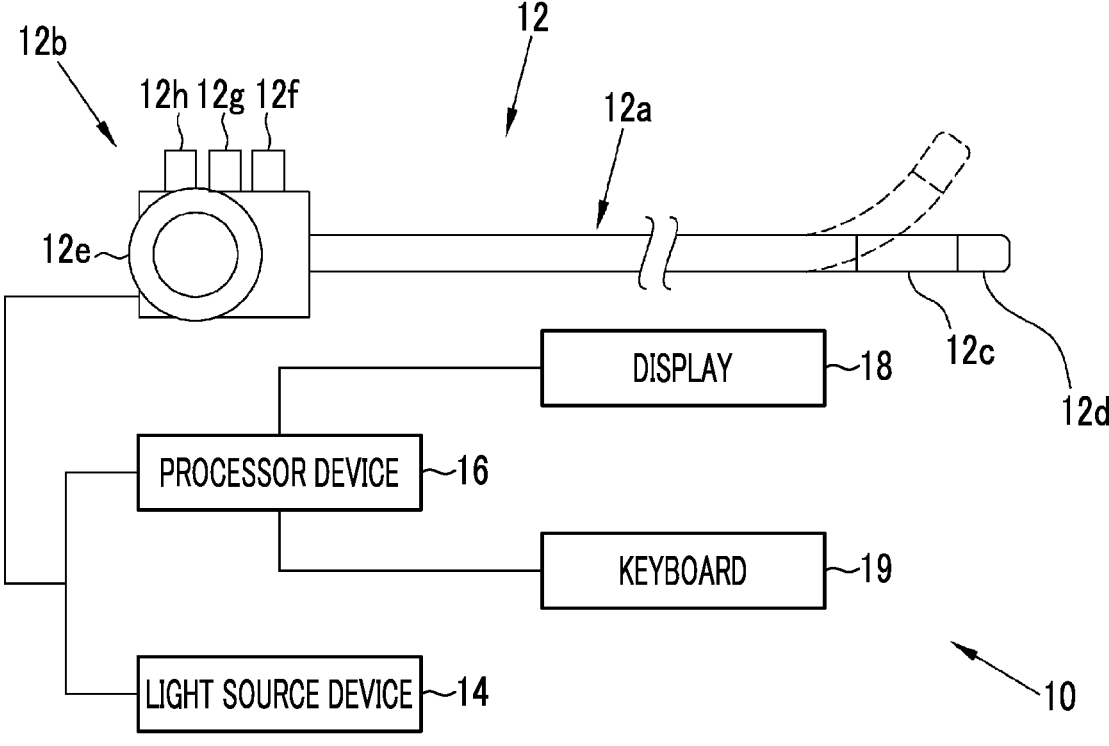
FIG. 1 is an explanatory view for describing a configuration of an endoscope system.

As shown in FIG. 1, an endoscope system 10 comprises an endoscope 12, a light source device 14, a processor device 16, a display 18, and a keyboard 19. The endoscope 12 images an observation target. The light source device 14 emits illumination light with which the observation target is irradiated. The processor device 16 performs system control of the endoscope system 10. The display 18 is a display unit that displays a display image based on an endoscope image, diagnosis support information, and the like. The keyboard 19 is an input device that performs setting input or the like into the processor device 16 or the like.

The endoscope system 10 includes, as observation modes, three modes including a normal observation mode, a special observation mode, and a diagnosis support mode in the present embodiment. In the normal observation mode, by irradiating an observation target with normal light such as white light and imaging the observation target, a normal observation image having a natural hue is displayed on the display 18 as a display image. In the special observation mode, by illuminating an observation target with normal light and special light having a different wavelength range or a different optical spectrum and imaging the observation target, a special image, in which a specific structure or the like of the observation target is enhanced, is displayed on the display 18 as a display image. In the diagnosis support mode, in addition to displaying the display image on the display 18, diagnosis support information is obtained and a doctor or the like, who is a user of the endoscope system 10, is notified of the obtaining. The notification of the diagnosis support information is performed by displaying on the display 18 or through other methods. In a case of displaying on the display 18, for example, the notification may be performed by superimposing on the display image or displaying on the display 18 separately from the display image.

The endoscope 12 has an insertion part 12a inserted into the body of a subject having an observation target, an operating part 12b provided at a proximal end portion of the insertion part 12a, a bendable part 12c provided at a distal end side of the insertion part 12a, and a distal end part 12d.

The bendable part 12c bends by operating an angle knob 12e of the operating part 12b. As a result, the distal end part 12d is directed in a desired direction. In addition, at the operating part 12b, a treatment tool insertion port (not shown), a scope button No. 1 12f, a scope button No. 2 12g, and a zoom operation part 12h are provided, in addition to the angle knob 12e. The treatment tool insertion port is an entrance into which a treatment tool, such as biopsy forceps, a snare, and an electric scalpel, is inserted. The treatment tool inserted into the treatment tool insertion port protrudes from the distal end part 12d. Various types of operations can be assigned to the scope buttons. For example, the scope button No. 1 12f is a freeze button and is used in an operation of acquiring a still image. The scope button No. 2 12g is used in an operation of switching observation modes. By operating the zoom operation part 12h, the observation target can be imaged while magnified or reduced.

Figure 2:
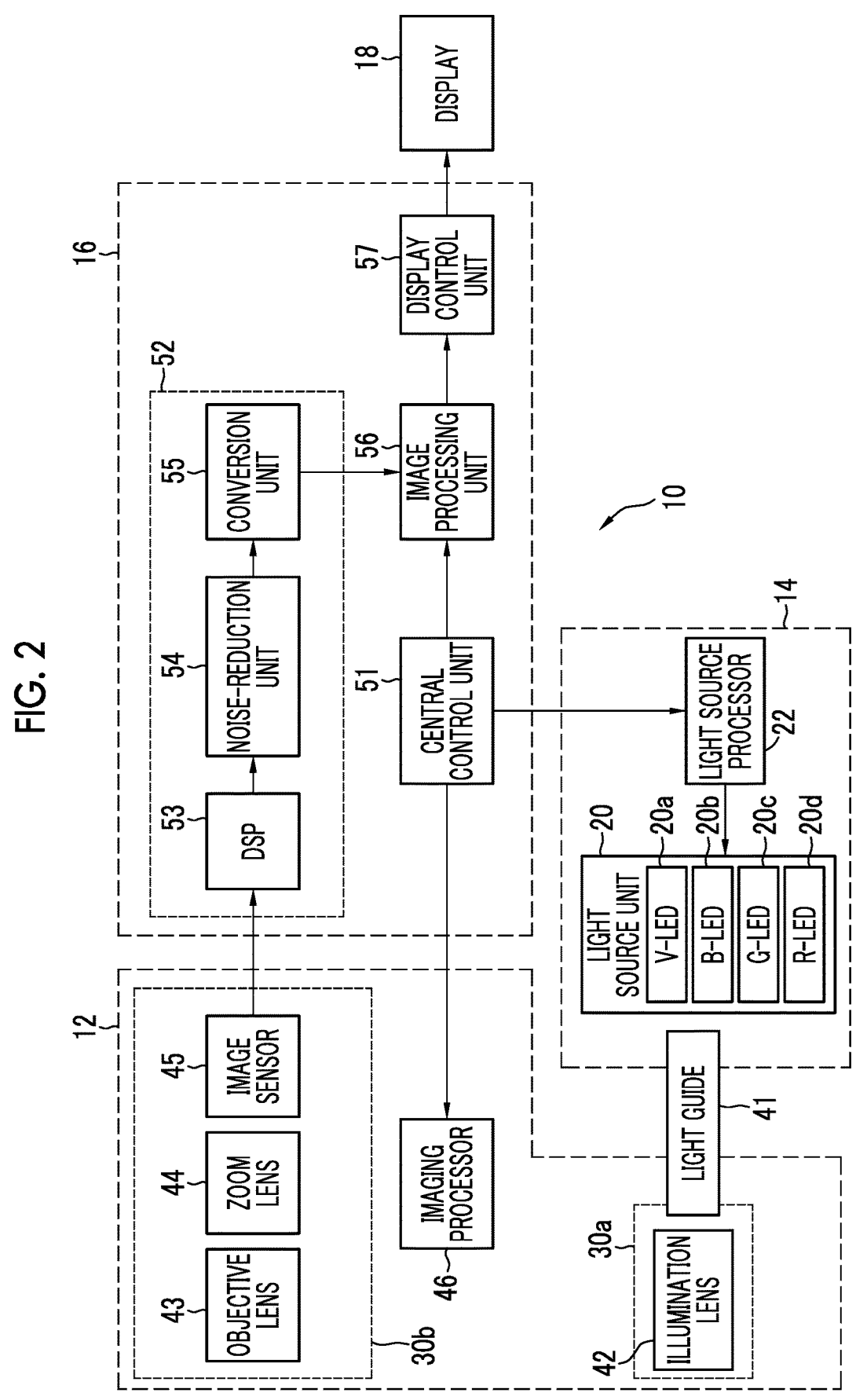
FIG. 2 is a block diagram showing a function of the endoscope system.

As shown in FIG. 2, the light source device 14 comprises a light source unit 20 that comprises a light source which emits illumination light and a light source processor 22 that controls an operation of the light source unit 20. The light source unit 20 emits illumination light that illuminates an observation target. The illumination light includes emission of light such as excitation light used in order to emit illumination light. The light source unit 20 includes a light source such as a laser diode, a light emitting diode (LED), a xenon lamp, and a halogen lamp and emits at least white illumination light (hereinafter, referred to as white light) or excitation light used in order to emit white light. The color of white includes a so-called color of pseudo-white that is substantially equivalent to white in imaging of an observation target using the endoscope 12.

The light source unit 20 includes, as necessary, a fluorescent body that emits light by being irradiated with excitation light or an optical filter that adjusts a wavelength range, an optical spectrum, or a light amount of illumination light or excitation light. In addition, the light source unit 20 can emit illumination light consisting of at least light with a narrowband (hereinafter, referred to as narrowband light). The term "narrowband" refers to a substantially almost single wavelength range in a relationship of characteristics of an observation target and/or spectral characteristics of a color filter included in an image sensor (image pick-up sensor) 45. For example, in a case where a wavelength range is approximately ±20 nm or lower (preferably approximately ±10 nm or lower), the light is narrowband light.

In addition, the light source unit 20 can emit a plurality of types of illumination light having optical spectra different from each other. The plurality of types of illumination light may include narrowband light. In addition, the light source unit 20 can emit, for example, light having a specific wavelength range or a specific optical spectrum, which is necessary in capturing an image used in order to calculate biological information such as oxygen saturation of hemoglobin included in an observation target.

Figure 3:
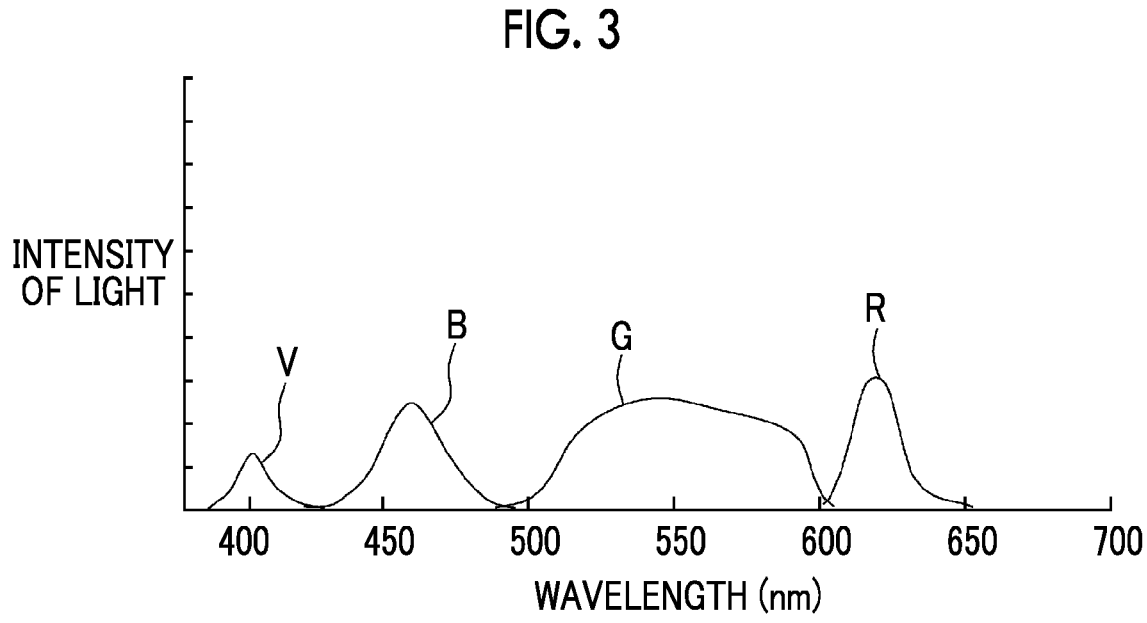
FIG. 3 is a graph showing optical spectra of violet light V, blue light B, green light G, and red light R.

In the present embodiment, the light source unit 20 has four colors of LEDs including a V-LED 20a, a B-LED 20b, a G-LED 20c, and an R-LED 20d. As shown in FIG. 3, the V-LED 20a emits violet light V having a central wavelength of 405 nm and a wavelength range of 380 to 420 nm. The B-LED 20b emits blue light B having a central wavelength of 460 nm and a wavelength range of 420 to 500 nm. The G-LED 20c emits green light G having a wavelength range of 480 to 600 nm. The R-LED 20d emits red light R having a central wavelength of 620 to 630 nm and a wavelength range of 600 to 650 nm. The central wavelengths of the V-LED 20a and the B-LED 20b have a range of approximately ±20 nm, preferably approximately ±5 nm to approximately ±10 nm. The violet light V is light having a short wavelength used in order to display and enhance superficial blood vessels, dense portions of superficial blood vessels, intramucosal bleeding, extramucosal bleeding, and the like used in the special observation mode or the diagnosis support mode and preferably includes 410 nm in a central wavelength or a peak wavelength. In addition, it is preferable that the violet light V and/or the blue light B is narrowband light.

The light source processor 22 controls turning on or off of each of light sources configuring the light source unit 20, a timing of shielding, intensity of light or a light emission amount, and the like. As a result, the light source unit 20 can emit a plurality of types of illumination light having different optical spectra in a period set in advance and by a light emission amount set in advance. In the present embodiment, the light source processor 22 controls turning on and off of the V-LED 20a, the B-LED 20b, the G-LED 20c, and the R-LED 20d, the intensity of light or a light emission amount in a case of turning on, insertion or removal of an optical filter, or the like by inputting each independent control signal. The light source processor 22 can emit the violet light V, the blue light B, the green light G, or the red light R while changing intensity of light or a light amount for unit time independently of each other by independently controlling each of the LEDs 20a to 20d. Therefore, the light source processor 22 can emit the plurality of types of illumination light having optical spectra different from each other and emit, for example, white illumination light, a plurality of types of illumination light having different optical spectra, illumination light consisting of at least narrowband light, or the like.

In a case of the normal observation mode, the light source processor 22 controls each of the LEDs 20a to 20d such that white light having a ratio of intensity of light between the violet light V, the blue light B, the green light G, and the red light R of Vc:Bc:Gc:Rc is emitted. Each of Vc, Bc, Gc, or Rc is larger than zero (0) and is not 0.

In addition, in a case of the special observation mode, the light source processor 22 controls each of the LEDs 20a to 20d such that special light having a ratio of intensity of light between the violet light V, the blue light B, the green light G, and the red light R of Vs:Bs:Gs:Rs is emitted as narrowband light having a small wavelength. The ratio of intensity of light of Vs:Bs:Gs:Rs is different from the ratio of intensity of light of Vc:Bc:Gc:Rc used in a case of the normal observation mode and is determined as appropriate depending on an observation object. Therefore, the light source unit 20 can emit a plurality of types of special light having optical spectra different from each other through control of the light source processor 22. For example, in a case of enhancing superficial blood vessels, it is preferable that Vs is larger than other Bs, Gs, and Rs, and in a case of enhancing middle-deep blood vessels, it is preferable that Gs is larger than other Vs, Bs, and Rs.

In the present specification, a case where a ratio of intensity of light excluding Vc, Bc, Gc, or Rc is such that a ratio of at least one semiconductor light source is zero (0) is included. Therefore, a case where any one or two or more of semiconductor light sources are not turned on is included. For example, as in a case where a ratio of intensity of light between the violet light V, the blue light B, the green light G, and the red light R is 1:0:0:0, also a case where only one semiconductor light source is turned on and other three semiconductor light sources are not turned on has a ratio of intensity of light.

In addition, in the present embodiment, it is preferable that the light source processor 22 automatically switches and emits a plurality of types of illumination light having optical spectra different from each other in order to acquire a plurality of types of candidate images in a case of the diagnosis support mode. It is preferable that each of the plurality of types of illumination light is repeatedly emitted in order set in advance. For this reason, it is preferable that each of the plurality of types of illumination light forms a specific pattern consisting of order set in advance, and illumination light is repeatedly emitted in the specific pattern.

For example, specifically, the light source processor 22 emits first illumination light in a first light emission pattern in a first illumination period and emits second illumination light in a second light emission pattern in a second illumination period. Illumination light emitted in the first illumination period is the first illumination light, and illumination light emitted in the second illumination period is the second illumination light. Since an endoscope image used for a display image is obtained, it is preferable that the first illumination light is white light. On the other hand, it is preferable that the second illumination light is special light with which an image suitable for a computer to perform a specific analysis process by illuminating an observation target is obtained as used in a recognition process. For example, in a case of performing an analysis process related to superficial blood vessels, it is preferable that the second illumination light is the violet light V. The first illumination light and the second illumination light may include a plurality of types of illumination light having optical spectra different from each other.

The first light emission pattern is light emission order of first illumination light, the second light emission pattern is light emission order of second illumination light, and elements configuring each light emission pattern is a frame which is a unit of an image. The frame refers to a period including at least a period from a specific timing for the image sensor 45 to a signal readout completion. Imaging and image acquisition are performed once in one frame. Any one of the first illumination light or the second illumination light is emitted, and both are not simultaneously emitted. One light emission period consists of at least one first light emission pattern and one second light emission pattern, and the first light emission pattern and the second light emission pattern configure a light emission period in combination. Illumination is performed by repeating the light emission period. Therefore, the light source unit 20 repeatedly emits each of a plurality of types of illumination light having optical spectra different from each other in the light emission period consisting of order set in advance. Details of the number of frames configuring each of the first light emission pattern or the second light emission pattern, the type of illumination light, or the like are set in advance.

Figure 4:
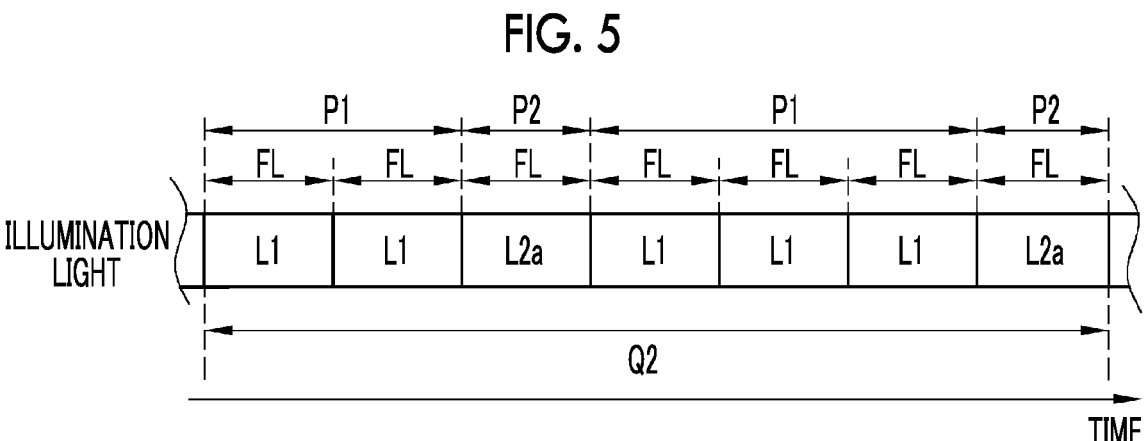
FIG. 4 is an explanatory view for describing a first A light emission pattern and a second A light emission pattern.

For example, it is preferable that the first light emission pattern is a first A light emission pattern or a first B light emission pattern. As shown in FIG. 4, in the first A light emission pattern, the number of frames FL of first illumination light L1 in a first illumination period P1 is the same in each first illumination period P1. Therefore, in a light emission period Q1, the number of the frames FL of the first illumination light L1 in the first illumination period P1 is set to two in total. As shown in FIG. 5, in the first B light emission pattern, the number of the frames FL in the first illumination period P1 is different in each first illumination period P1. Therefore, in a light emission period Q2, a case where the number of the frames FL of the first illumination light L1 in the first illumination period P1 is two and a case where the number is three are included. In the first A light emission pattern and the first B light emission pattern, the first illumination light L1 has the same optical spectrum and is white light.

It is preferable that the second light emission pattern is a second A light emission pattern, a second B light emission pattern, a second C light emission pattern, or a second D light emission pattern. As shown in FIG. 4, in the second A light emission pattern, the number of the frames FL of second illumination light L2*a* in a second illumination period P2 is the same in each second illumination period P2. Therefore, in the light emission period Q1, the number of the frames FL of the second illumination light L2*a* in the second illumination period P2 is set to one in total. Second illumination light L2 includes illumination light rays having different optical spectra in some cases, the illumination light rays are distinguished by describing them as the second illumination light L2*a* and second illumination light L2*b*, and a case of being described as the second illumination light L2, the second illumination light L2*a* and the second illumination light L2*b* are collectively referred to. Therefore, in a case where the second illumination light L2 is the second illumination light L2*b* in the second A light emission pattern, and the second illumination light L2*b* is emitted in one frame FL in the second illumination period P2. As shown in FIG. 5, also in the light emission period Q2, the second illumination light L2 is emitted in the second A light emission pattern as in the light emission period Q1.

As shown in FIG. 6, in the second B light emission pattern, in a light emission period Q3, the number of the frames FL of the second illumination period P2 is the same in each second illumination period P2, and the optical spectrum of the second illumination light L2 is the second illumination light L2*a* or the second illumination light L2*b* in each second illumination period P2, which means different from each other. As shown in FIG. 7, in the second C light emission pattern, in a light emission period Q4, the number of the frames FL of the second illumination period P2 is different in each second illumination period P2, and the optical spectrum of the second illumination light L2 is the second illumination light L2*a* in each second illumination period P2, which means the same.

As shown in FIG. 8, in the second D light emission pattern, in a light emission period Q5, the number of the frames FL of the second illumination period P2 is different in each second illumination period P2, and the optical spectrum of the second illumination light L2 is the second illumination light L2*a* or the second illumination light L2*b* in each second illumination period P2, which means different from each other.

As described above, in a case of the diagnosis support mode, the light source processor 22 repeats the light emission period configured by combining the first light emission pattern and the second light emission pattern. As shown in FIG. 4, the light emission period Q1 consists of the first A light emission pattern and the second A light emission pattern. As shown in FIG. 5, the light emission period Q2 consists of the first B light emission pattern and the second A light emission pattern. As shown in FIG. 6, the light emission period Q3 consists of the first A light emission pattern and the second B light emission pattern. As shown in FIG. 7, the light emission period Q4 consists of the first A light emission pattern and the second C light emission pattern. As shown in FIG. 8, the light emission period Q5 consists of the first A light emission pattern and the second D light emission pattern. In the first light emission pattern, the optical spectrum of the first illumination light L1 may be different in each first illumination period P1.

In addition, in a case of the diagnosis support mode, the light source processor 22 may change the first light emission pattern or the second light emission pattern based on an analysis process result from each analysis process to be described later. The change of the light emission pattern includes a change in the type of illumination light. Specifically, for example, based on the analysis process result, switching the second light emission pattern, in which a second A pattern is changed to the second B light emission pattern or the second A light emission pattern using the second illumination light L2*a* is changed to the second A light emission pattern using the second illumination light L2*b*, or the like, may be performed.

Herein, the first illumination period P1 is preferably longer than the second illumination period P2, and the first illumination period P1 is preferably two frames or more. For example, in FIG. 4, in the light emission period Q1 when the first light emission pattern is a first A light emission pattern and the second light emission pattern is the second A light emission pattern, the first illumination period P1 is two frames, and the second illumination period P2 is one frame. Since the first illumination light L1 is used in generating a display image displayed on the display 18, it is preferable that a bright display image is obtained by illuminating an observation target with the first illumination light L1.

As shown in FIG. 2, light emitted by each of the LEDs 20*a* to 20*d* is incident to a light guide 41 via an optical path combining unit (not shown) composed of a mirror, a lens, or the like. The light guide 41 is built into the endoscope 12 and a universal cord (not shown). The universal cord is a cord that connects the endoscope 12 to the light source device 14 and the processor device 16. The light guide 41 transmits light from the optical path combining unit to the distal end part 12*d* of the endoscope 12.

An illumination optical system 30*a* and an imaging optical system 30*b* are provided at the distal end part 12*d* of the endoscope 12. The illumination optical system 30*a* has an illumination lens 42, and illumination light transmitted by the light guide 41 is emitted toward an observation target via the illumination lens 42.

The imaging optical system 30*b* has an objective lens 43, a zoom lens 44, and the image sensor 45. The image sensor 45 images an observation target using reflected light of illumination light returning from the observation target or the like (including scattered light, fluorescence emitted by the observation target, or fluorescence attributable to drug administered or the like to the observation target, or the like, in addition to the reflected light) via the objective lens 43 and the zoom lens 44. The zoom lens 44 moves as the zoom operation part 12*h* operates, and an observation target image is magnified or reduced.

The image sensor 45 has one color of color filter among a plurality of colors of color filters, for each pixel. In the present embodiment, the image sensor 45 is a color sensor having a primary color system color filter. Specifically, the image sensor 45 has an R pixel having a red color filter (R filter), a G pixel having a green color filter (G filter), and a B pixel having a blue color filter (B filter).

As the image sensor 45, a charge coupled device (CCD) sensor or a complementary metal oxide semiconductor (CMOS) sensor can be used. In addition, the image sensor 45 of the present embodiment is a primary color system color sensor, but a complementary color system color sensor can also be used. The complementary color system color sensor has, for example, a cyan pixel provided with a cyan color filter, a magenta pixel provided with a magenta color filter, a yellow pixel provided with a yellow color filter, and a green pixel provided with a green color filter. In a case where color conversion of complementary color-primary color is performed on an image obtained from each of the color pixels in a case of using the complementary color system color sensor, the image can be converted into an image which is the same as an image obtained with the primary color system color sensor. The same also applies to a case of having one or a plurality of types of pixels having characteristics other than the above, such as a W pixel (a white pixel receiving light in almost the entire wavelength range), in the primary color system sensor or the complementary color system sensor. In addition, the image sensor 45 of the present embodiment is a color sensor, but a monochrome sensor that does not have a color filter may be used.

The endoscope 12 comprises an imaging processor 46 that controls the image sensor 45. Control by the imaging processor 46 is different for each observation mode. In the normal observation mode, the imaging processor 46 controls the image sensor 45 such that an observation target illuminated with normal light is imaged. Accordingly, a Bc image signal is output from the B pixel of the image sensor 45, a Gc image signal is output from the G pixel, and an Rc image signal is output from the R pixel.

In the special observation mode, the imaging processor 46 controls the image sensor 45 such that an observation target illuminated with special light is imaged. Accordingly, a Bs image signal is output from the B pixel of the image sensor 45, a Gs image signal is output from the G pixel, and an Rs image signal is output from the R pixel.

In the diagnosis support mode, the imaging processor 46 controls the image sensor 45 such that an observation target illuminated with the first illumination light L1 or the second illumination light L2 is imaged. Accordingly, for example, in a case of illuminating with the first illumination light L1, a B1 image signal is output from the B pixel of the image sensor 45, a G1 image signal is output from the G pixel of the image sensor 45, and an R1 image signal is output from the R pixel of the image sensor 45. In addition, in a case of illuminating with the second illumination light L2, for example, a B2 image signal is output from the B pixel of the image sensor 45, a G2 image signal is output from the G pixel of the image sensor 45, and an R2 image signal is output from the R pixel of the image sensor 45.

In the processor device 16, a program related to a process or the like performed by a central control unit 51, an image acquisition unit 52, an image processing unit 56, a display control unit 57, and the like, which are to be described later, is incorporated into a memory (not shown). By operating the program with the central control unit 51 composed of an image processor included in the processor device 16 functioning as the image processing apparatus, functions of the central control unit 51, the image acquisition unit 52, the image processing unit 56, and the display control unit 57 are realized.

The central control unit 51 performs overall control of the endoscope system 10 such as synchronization control of an irradiation timing of illumination light and an imaging timing. In a case of inputting various types of setting using the keyboard 19 and the like, the central control unit 51 inputs the setting into each unit of the endo scope system 10, such as the light source processor 22, the imaging processor 46, and the image processing unit 56.

The image acquisition unit 52 acquires, from the image sensor 45, a captured image of an observation target using each color pixel, that is, an RAW image. In addition, the RAW image is an image (endoscope image) before performing a demosaicing process. Insofar as an image is an image before performing a demosaicing process, the RAW image includes also an image obtained by performing any process such as a noise reducing process on an image acquired from the image sensor 45.

The image acquisition unit 52 comprises a digital signal processor (DSP) 53, a noise-reduction unit 54, and a conversion unit 55, in order to perform various types of processes on an acquired RAW image as necessary.

The DSP 53 comprises, for example, an offset processing unit, a defect correction processing unit, a demosaicing processing unit, a linear matrix processing unit, a YC conversion processing unit, and the like (none of which are shown). The DSP 53 performs various types of processes on an RAW image using the units or an image generated using the RAW image.

The offset processing unit performs an offset process on an RAW image. The offset process is a process in which a dark current component is reduced from the RAW image, and an accurate zero level is set. The offset process is referred to as a clamping process in some cases. The defect correction processing unit performs a defect correction process on the RAW image. The defect correction process is a process of correcting or generating a pixel value of a RAW pixel corresponding to the defective pixel of the image sensor 45 in a case where the image sensor 45 includes a pixel (defective pixel) having a defect attributable to a manufacturing step or a change with time.

The demosaicing processing unit performs a demosaicing process on an RAW image having each color corresponding to each color of color filter. The demosaicing process is a process of generating a missing pixel value attributable to arrangement of color filters in the RAW image by interpolation. The linear matrix processing unit performs a linear matrix process on an endoscope image generated by assigning one or a plurality of RAW images to a channel of each color of RGB. The linear matrix process is a process for improving color reproduction of the endoscope image. A YC conversion process performed by the YC conversion processing unit is a process of converting an endoscope image generated by assigning one or a plurality of RAW images to a channel of each color of RGB into an endoscope image having a luminance channel Y, a color difference channel Cb, and a color difference channel Cr.

The noise-reduction unit 54 performs a noise reducing process on an endoscope image having the luminance channel Y, the color difference channel Cb, and the color difference channel Cr, using, for example, a moving averaging method, a median filter method, or the like. The conversion unit 55 reconverts the luminance channel Y, the color difference channel Cb, and the color difference channel Cr after the noise reducing process into an endoscope image having a channel of each color of BGR again.

Figure 9:
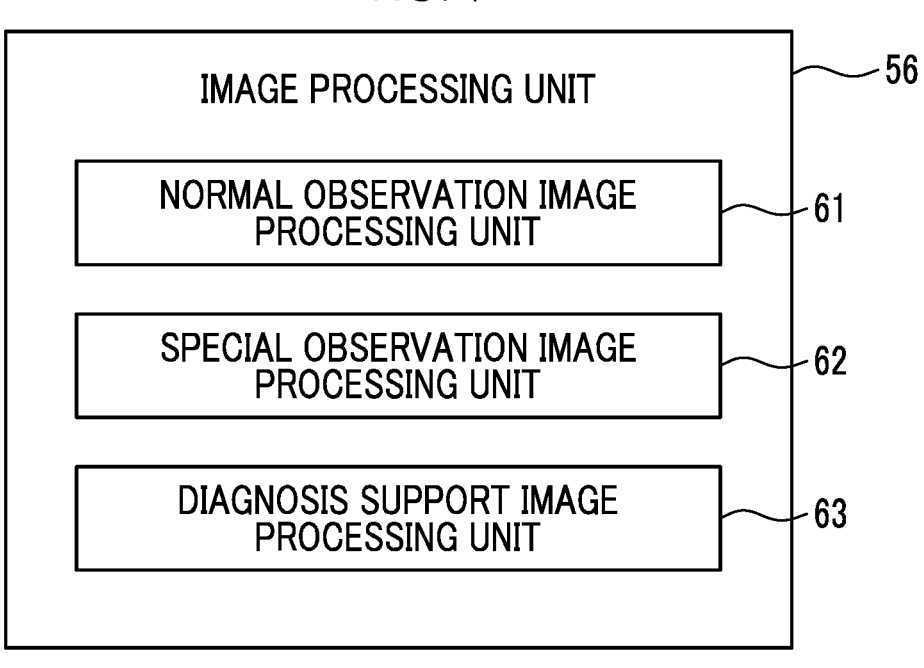
FIG. 9 is a block diagram showing a function of an image processing unit.

The image processing unit 56 performs a necessary image process or operation on an endoscope image output by the image acquisition unit 52. As shown in FIG. 9, the image processing unit 56 comprises a normal observation image processing unit 61, a special observation image processing unit 62, and a diagnosis support image processing unit 63. The normal observation image processing unit 61 performs an image process for a normal observation image on the input Rc image signal, the input Gc image signal, and the input Bc image signal for one frame. The image process for a normal observation image includes a color conversion process such as a 3×3 matrix process, a gradation conversion process, and a three-dimensional look up table (LUT) process and a structure enhancement process such as a color enhancement process and spatial frequency enhancement. The Rc image signal, the Gc image signal, and the Bc image signal, on which the image process for a normal observation image is performed, are normal observation images and are input into the display control unit 57 as display images in the normal observation mode.

The special observation image processing unit 62 performs an image process for a special observation image on the input Rs image signal, the input Gs image signal, and the input Bs image signal for one frame. The image process for a special observation image includes a color conversion process such as a 3×3 matrix process, a gradation conversion process, and a three-dimensional look up table (LUT) process and a structure enhancement process such as a color enhancement process and spatial frequency enhancement. The Rs image signal, the Gs image signal, and the Bs image signal, on which the image process for a special observation image is performed, are special observation images and are input into the display control unit 57 as display images in the special observation mode.

Figure 10:
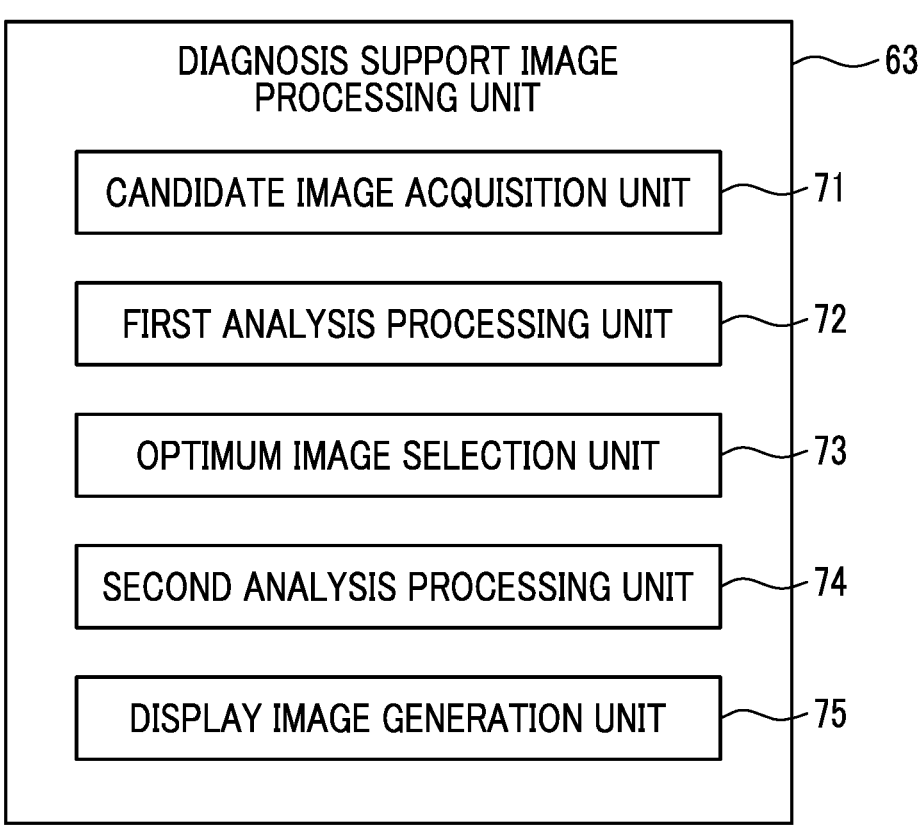
FIG. 10 is a block diagram showing a function of a diagnosis support image processing unit.

The diagnosis support image processing unit 63 performs an image analysis process and the like in the diagnosis support mode and generates diagnosis support information. The diagnosis support information indicates a user such as a doctor. As shown in FIG. 10, the diagnosis support image processing unit 63 comprises a candidate image acquisition unit 71, a first analysis processing unit 72, an optimum image selection unit 73, a second analysis processing unit 74, and a display image generation unit 75.

The candidate image acquisition unit 71 generates and acquires a plurality of types of candidate images based on an endoscope image output by the image acquisition unit 52. The type of candidate image is distinguished by any one or both of the next two points. The first point is distinguishing by the optical spectrum of illumination light in a case of imaging an observation target. Therefore, the candidate image acquisition unit 71 acquires an endoscope image obtained by imaging an observation target illuminated with each of a plurality of types of illumination light emitted by the light source unit, which have optical spectra different from each other, as each type of candidate image. The second point is distinguishing by a method of an image process (hereinafter, referred to as an image process for candidate image generation) for generating a candidate image with respect to an endoscope image.

Examples of the method of the image process for candidate image generation include a method of an image process such as an enhancement process and specifically include a color difference extension process and/or a structure enhancement process. A case of distinguishing between candidate images through the method of the image process for candidate image generation includes not performing the image process for candidate image generation. Therefore, also an endoscope image output by the image acquisition unit 52, on which the image process for candidate image generation is not performed, is one type of candidate image. Therefore, even in a case where a combination of the optical spectrum of illumination light and the image process for candidate image generation is different, the endoscope image is one type of candidate image. A candidate image in which any one of the optical spectrum of illumination light or the image process is different is a different type of candidate image.

Figure 11:
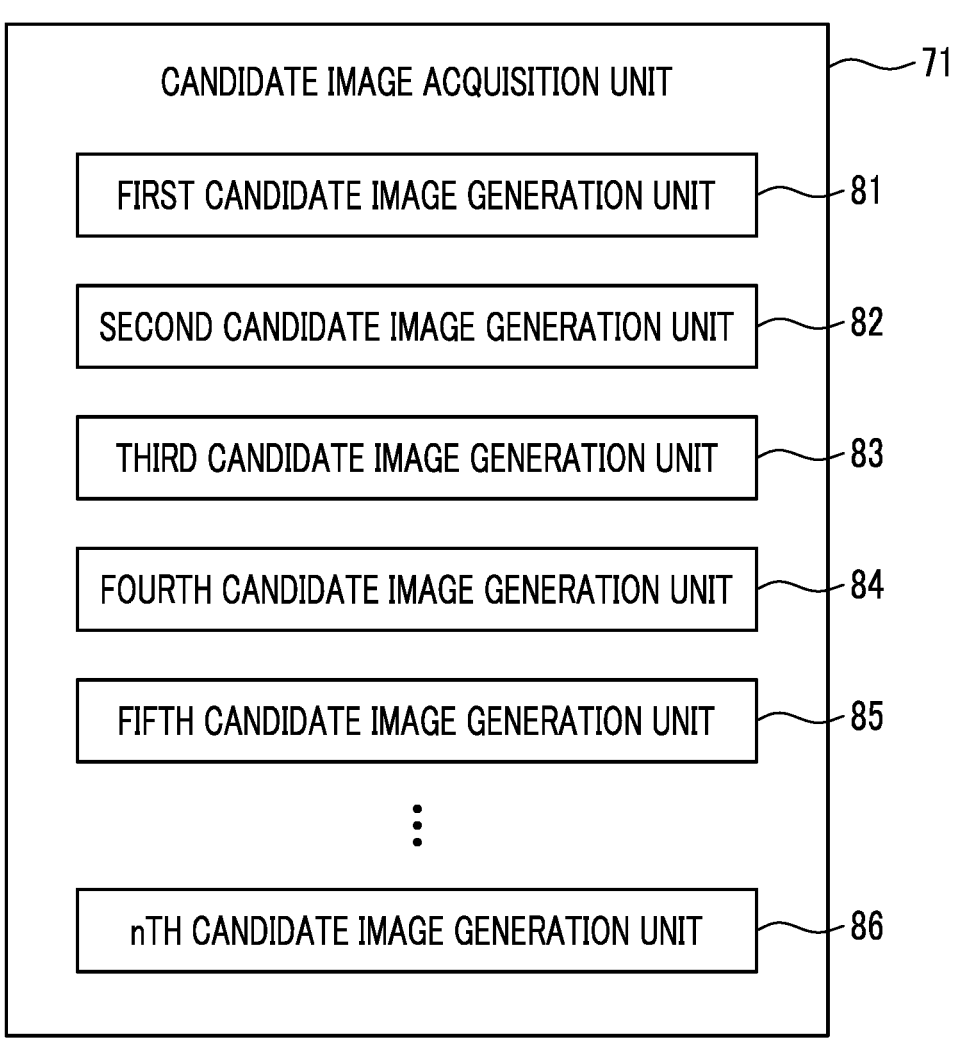
FIG. 11 is a block diagram showing a function of a candidate image acquisition unit.

As shown in FIG. 11, the candidate image acquisition unit 71 comprises each candidate image generation unit that generates each of a plurality of types of candidate images. For example, the candidate image acquisition unit 71 comprises a first candidate image generation unit 81, a second candidate image generation unit 82, a third candidate image generation unit 83, a fourth candidate image generation unit 84, a fifth candidate image generation unit 85, and an nth candidate image generation unit 86. n is an integer that is 6 or more. n can be set depending on the number of the plurality of types of candidate images. Each candidate image acquisition unit performs each image process for illumination light and/or candidate image generation below.

The first candidate image generation unit 81 performs an image process for a first candidate image (hereinafter, referred to as a first image process) for generating a first candidate image. The first image process is a process performed on the B1 image signal, the G1 image signal, and the R1 image signal obtained by emitting first illumination light that is white light, which is a first illumination light optical spectrum. The first image process is the same as a normal display image process of the normal observation image processing unit 61 and obtains the same first candidate image as a normal display image. The first candidate image is one type of candidate image. Therefore, the candidate image acquisition unit 71 acquires an image obtained by imaging an observation target illuminated with white illumination light as one type of candidate image.

Figure 12:
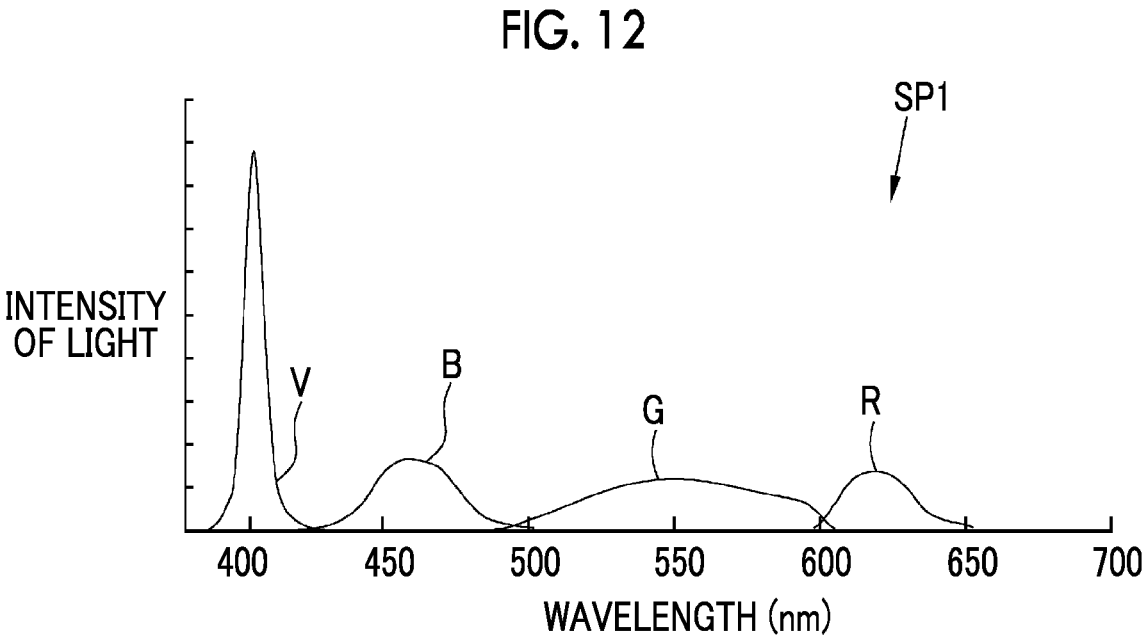
FIG. 12 is a graph showing a second illumination light optical spectrum SP1.

The second candidate image generation unit 82 performs an image process for a second candidate image (hereinafter, referred to as a second image process) for generating a second candidate image. The second image process is a process performed on the B2 image signal, the G2 image signal, and the R2 image signal obtained by emitting the second illumination light L2 in a second illumination light optical spectrum SP1. As shown in FIG. 12, in the second illumination light L2 emitted in the second illumination light optical spectrum SP1, the violet light V is preferably light that has a peak intensity higher than peak intensities of the blue light B, the green light G, and the red light R, which have different colors. The second image process is a pseudo-color process of assigning the B2 image signal to a B channel and a G channel for display and assigning the G2 image signal to an R channel for display. Through the pseudo-color process, a second candidate image in which blood vessels having a specific depth, such as superficial blood vessels, or structures are enhanced is obtained. The second candidate image is one type of candidate image.

Figure 13:
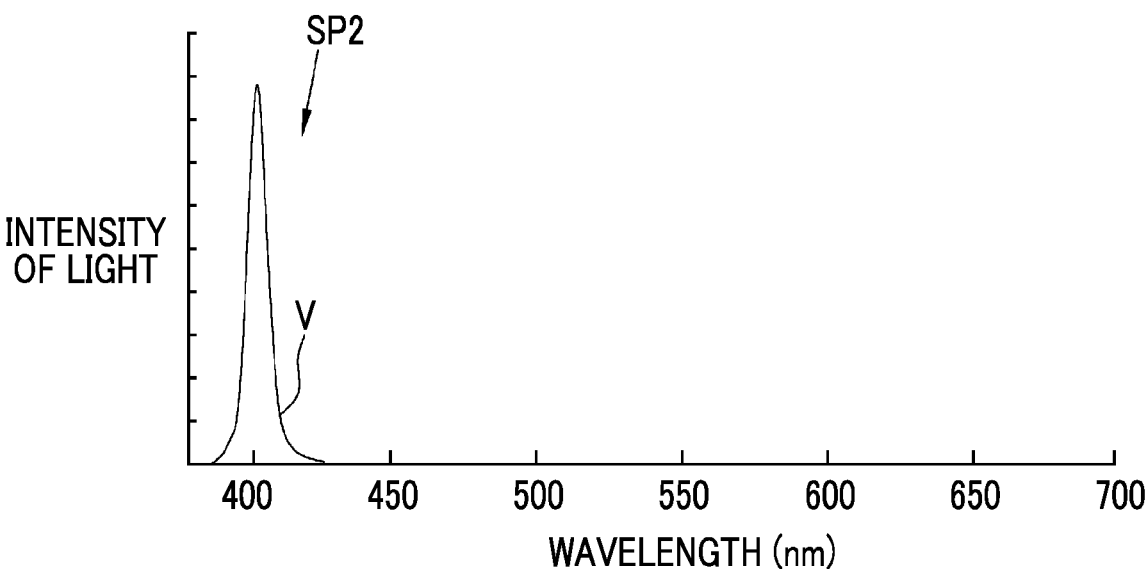
FIG. 13 is a graph showing a second illumination light optical spectrum SP2.

The third candidate image generation unit 83 performs an image process for a third candidate image (hereinafter, referred to as a third image process) for generating a third candidate image. The third image process is a process performed on the B2 image signal, the G2 image signal, and the R2 image signal obtained by emitting second illumination light in a second illumination light optical spectrum SP2. As shown in FIG. 13, the second illumination light emitted in the second illumination light optical spectrum SP2 is preferably only the violet light V (peak wavelength is, for example, 400 to 420 nm). The third image process is a process of assigning the B2 image signal to the B channel, the G channel, and the R channel for display and adjusting a tone and gradation balance. Through the third image process, a third candidate image in which extremely superficial blood vessels shallower than superficial blood vessels or the like are enhanced is obtained. The third candidate image is one type of candidate image.

Figure 14:
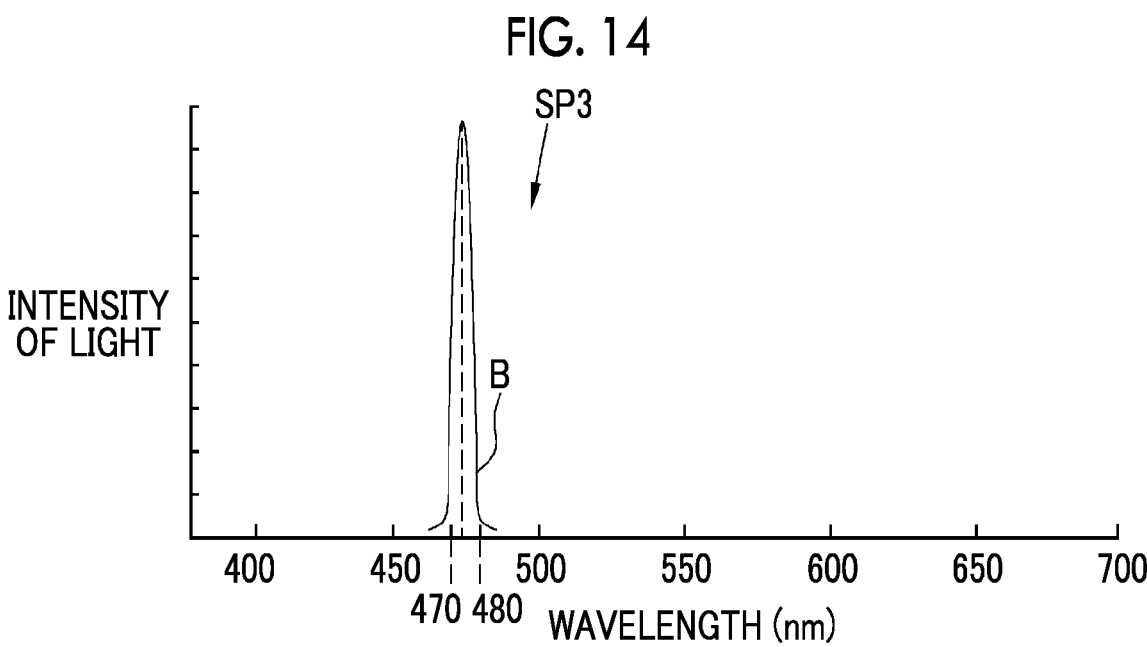
FIG. 14 is a graph showing a second illumination light optical spectrum SP3.

The fourth candidate image generation unit 84 performs an image process for a fourth candidate image (hereinafter, referred to as a fourth image process) for generating a fourth candidate image. The fourth image process is a process performed on the B2 image signal, the G2 image signal, and the R2 image signal obtained by emitting second illumination light in a second illumination light optical spectrum SP3, in addition to the B1 image signal, the G1 image signal, and the R1 image signal obtained by emitting first illumination light. As shown in FIG. 14, the second illumination light optical spectrum SP3 is preferably the blue light B (peak wavelength is, for example, 470 to 480 nm), which is light in a wavelength range having a difference in a light absorption coefficient between oxygenated hemoglobin and reduced hemoglobin.

Figure 15:
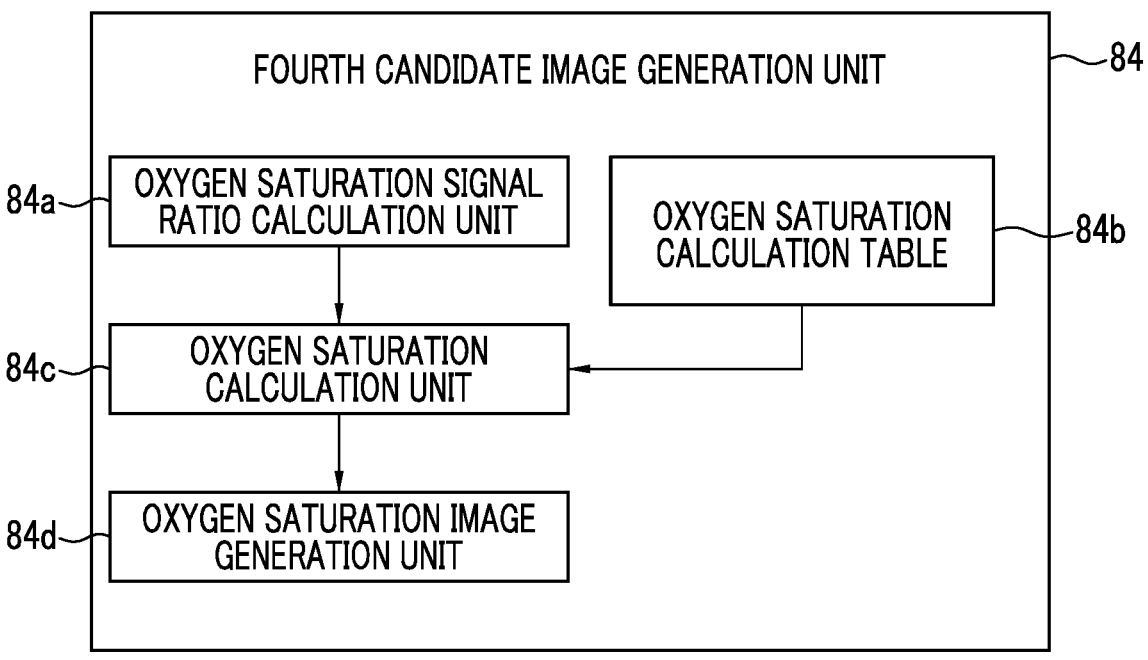
FIG. 15 is a block diagram showing a function of a fourth candidate image generation unit.

As shown in FIG. 15, the fourth candidate image generation unit 84 comprises an oxygen saturation signal ratio calculation unit 84*a* that performs a signal ratio calculation process of calculating a first signal ratio (B2/G1) representing a ratio between the B2 image signal and the G1 image signal and a second signal ratio (R1/G1) representing a ratio between the R1 image signal and G1 image signal, an oxygen saturation calculation unit 84*c* that calculates oxygen saturations corresponding to the first signal ratio and the second signal ratio with reference to an oxygen saturation calculation table 84*b,* and an oxygen saturation image generation unit 84*d* that generates an oxygen saturation image based on oxygen saturation. The oxygen saturation image is the fourth candidate image obtained through the fourth image process. The fourth candidate image is one type of candidate image.

Figure 16:
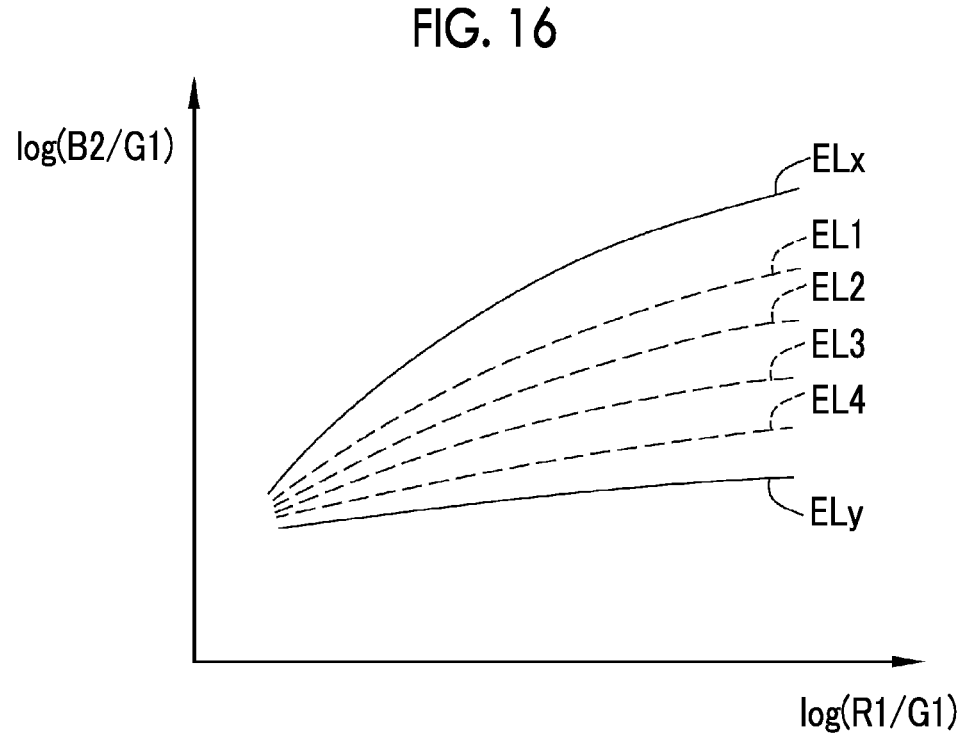
FIG. 16 is a graph showing an oxygen saturation calculation table.

The oxygen saturation calculation table 84*b* stores a correlation between oxygen saturation, and the first signal ratio and the second signal ratio. Specifically, as shown in FIG. 16, the oxygen saturation calculation table 84*b* is composed of a two-dimensional table in which isolines ELx, EL1, EL2, EL3, and ELy of oxygen saturation or the like are defined in a two-dimensional space with the first signal ratio (B2/G1) and the second signal ratio (R1/G1) as axes. For example, the isoline ELx indicates that oxygen saturation is 0%, the isoline EL1 indicates that oxygen saturation is 30%, the isoline EL2 indicates that oxygen saturation is 50%, and the isoline EL3 indicates that oxygen saturation is 80%. The positions and shapes of isolines with respect to the first signal ratio (B2/G1) and the second signal ratio (R1/G1) are obtained in advance through physical simulation of light scattering. The first signal ratio (B2/G1) and the second signal ratio (R1/G1) are preferably in a log scale.

Figure 17:
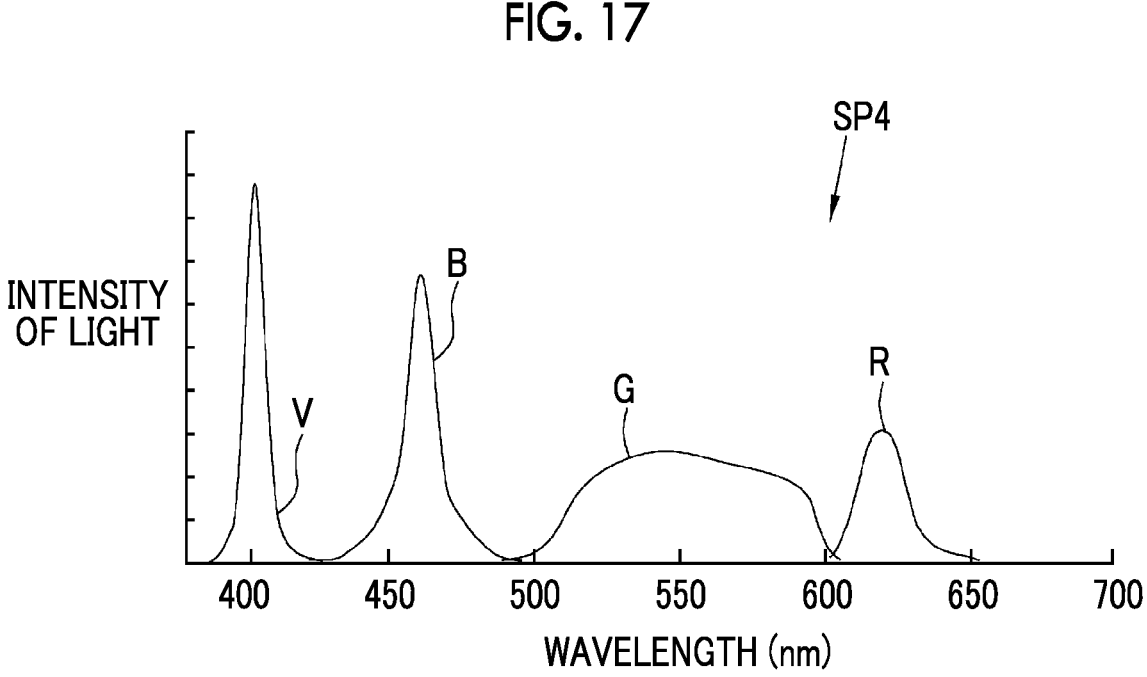
FIG. 17 is a graph showing a second illumination light optical spectrum SP4.

The fifth candidate image generation unit 85 performs an image process for a fifth candidate image (hereinafter, referred to as a fifth image process) for generating a fifth candidate image. The fifth image process is a color difference extension process and specifically is a process performed on the B2 image signal, the G2 image signal, and the R2 image signal obtained by emitting second illumination light in a second illumination light optical spectrum SP4. As shown in FIG. 17, the second illumination light optical spectrum SP4 is preferably light in which peak intensities of the violet light V and the blue light B are higher than peak intensities of the green light G and the red light R. In addition, it is preferable that the intensity of the red light R is high compared to the second illumination light optical spectrum SP2.

Figure 18:
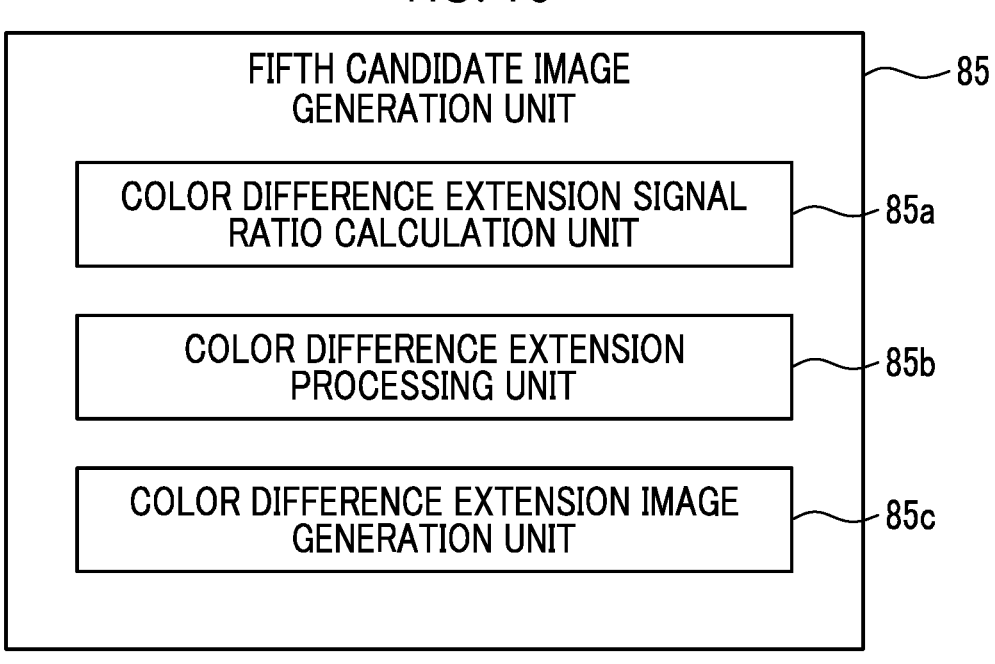
FIG. 18 is a block diagram showing a function of a fifth candidate image generation unit.

As shown in FIG. 18, in the fifth image process, a color difference extension signal ratio calculation unit 85*a* that performs a signal ratio calculation process of calculating a first signal ratio (B2/G2) representing a ratio between the B2 image signal and the G2 image signal and a second signal ratio (G2/R2) representing a ratio between the R2 image signal and the G2 image signal, a color difference extension processing unit 85*b* that performs a color difference extension process of extending a color difference between a plurality of observation target ranges based on the first signal ratio and the second signal ratio, and a color difference extension image generation unit 85*c* that generates a color difference extension image based on the first signal ratio and the second signal ratio after the color difference extension process are provided. The color difference extension image is the fifth candidate image obtained through the fifth candidate image generation unit 85. The fifth candidate image is one type of candidate image.

Figure 19:
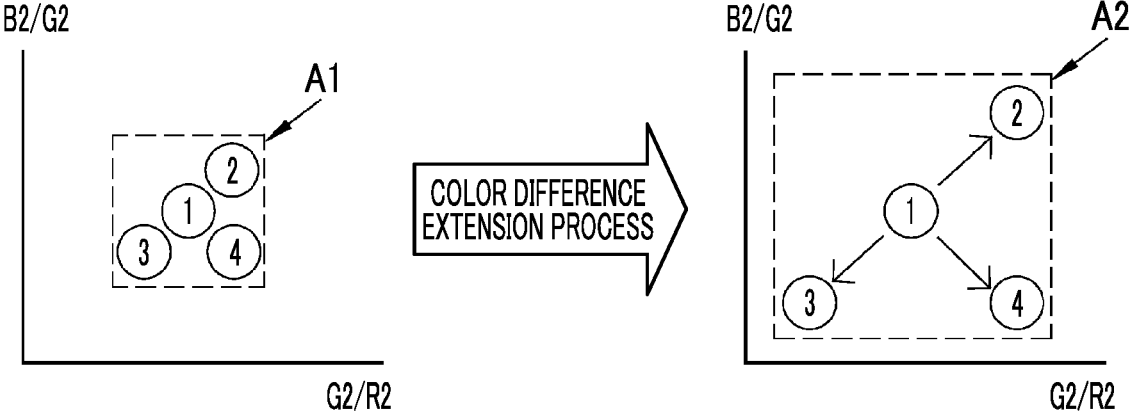
FIG. 19 is an explanatory view for describing a color difference extension process.

As shown in FIG. 19, in the color difference extension process, it is preferable to extend a distance between a plurality of observation target ranges in a two-dimensional space consisting of the first signal ratio (B2/G2) and the second signal ratio (G2/R2). Specifically, in the two-dimensional space, in a state where the position of a first range (indicated by 1 surrounded by a circle), among the plurality of observation target ranges, is maintained in the color difference extension process, it is preferable to extend a distance between the first range and a second range (indicated by 2 surrounded by a circle), a distance between the first range and a third range (indicated by 3 surrounded by a circle), and a distance between the first range and fourth range (indicated by 4 surrounded by a circle). It is preferable to perform the color difference extension process through a method of adjusting a radius vector and an angle, after transforming the first signal ratio and the second signal ratio into polar coordinates. It is preferable that the first range is a normal portion where there is no lesion or the like and the second to fourth ranges are abnormal portions having a possibility in which there is a lesion or the like. Since a range A1 in the two-dimensional space before the color difference extension process is expanded to a range A2 after the color difference extension process through the color difference extension process, an image in which a color difference is enhanced, for example, a color difference between the abnormal portion and the normal portion is enhanced is obtained.

As described above, a plurality of types of candidate images are generated by performing image processes of various types of methods on an endoscope image. The nth candidate image generation unit 86 generates the nth type of candidate image. The method or content of an image process is not limited to the above. For example, in addition to the color difference extension process, an enhancement process such as a structure enhancement process may be performed. The type of candidate image is distinguished by the presence or absence of the enhancement process or the type of enhancement process with respect to an endoscope image, and the distinguished candidate image is acquired as each type of candidate image. Any one image process of the first image process to the nth image process may be performed or may not be performed on an endoscope image on which an enhancement process is performed.

The structure enhancement process is a process that is performed on an acquired endoscope image such that the endoscope image becomes an endoscope image in which blood vessels in an observation target are enhanced and shown. Specifically, as an endoscope image, any one of the B1 image signal, the G1 image signal, or the R1 image signal obtained by emitting first illumination light or the B2 image signal, the G2 image signal, or the R2 image signal obtained by emitting second illumination light is used. In the structure enhancement process, a shade histogram which is a graph obtained by plotting a pixel value (brightness value) on the lateral axis and a frequency on the vertical axis in the acquired endoscope image is acquired, and gradation correction is performed through a gradation correction table stored in advance in a memory (not shown) of the image processing unit 56 or the like. The gradation correction table has the lateral axis representing an input value and the vertical axis representing an output value, has a gradation correction curve indicating a correspondence relationship between an input value and an output value and extends the dynamic range of the acquired endoscope image by performing gradation correction based on, for example, a substantially S-shaped gradation correction curve. Accordingly, in an original image before an enhancement process for structural enhancement, a portion having a low density has a lower density and a portion having a high density has a higher density. Thus, for example, a density difference between a blood vessel region and a region where a blood vessel does not exist increases, and contrast of blood vessels improves. Therefore, in an endoscope image processed through the structure enhancement process, the contrast of blood vessels is improved, visibility of a blood vessel structure is improved, and, for example, a region where a degree of density of blood vessels is high can be preferably used as a specific region in determination or the like more easily and accurately.

In addition, it is preferable that the candidate image acquisition unit 71 is configured to acquire an endoscope image obtained by illuminating an observation target with illumination light, which is emitted by the light source unit 20 and includes narrowband light in a wavelength range set in advance, and imaging the observation target as one type of candidate image. Therefore, it is preferable that a plurality of types of candidate images include at least one type of endoscope image generated with illumination light consisting of narrowband light. The endoscope image obtained by imaging the observation target illuminated with illumination light including the violet light V and/or the blue light B, which is preferably narrowband light, may be generated as one type of candidate image.

In addition, it is preferable that the narrowband of narrowband light is a short wave of 480 nm or less. Further, it is preferable that the central wavelength or peak wavelength of narrowband light includes a wavelength of 410 nm. Further, it is preferable that narrowband light is monochromatic light having only one narrowband. Further, it is preferable to acquire an endoscope image obtained by performing coloring on an endoscope image having narrowband light as a main component as one type of candidate image.

An endoscope image obtained by performing coloring on an endoscope image having narrowband light as a main component is obtained through a method of generating a color image from a specific color image, for example, by assigning specific color images obtained by imaging an observation target with specific monochromatic light to a plurality of color channels and adjusting a balance between the respective color channels. In this case, in coloring, it is preferable to magnify a distance between a color having a relatively low frequency component among observation target images of an observation target and a color having a relatively high frequency component among the observation target images in a L*a*b* color space. A candidate image based on such an endoscope image can be an endoscope image in which a specific fine structure such as blood vessels is more easily understood by adjusting coloring corresponding to the observation target image, for example, in a zoom image or the like. In addition, in addition to an endoscope image that is easily visible to humans, the candidate image can be an endoscope image with which a good analysis result is obtained through an analysis process based on a computer by adjusting coloring, which is preferable.

Figure 20:
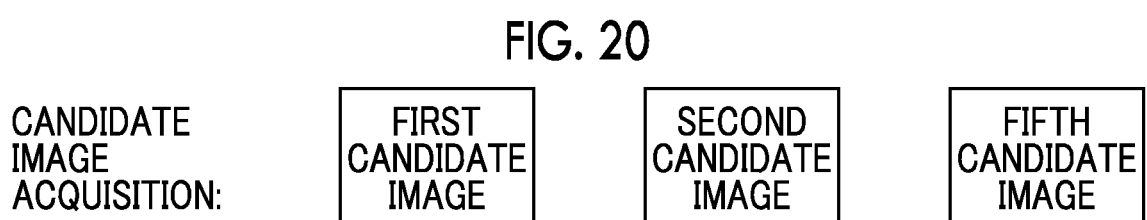
FIG. 20 is an explanatory view for describing candidate image acquisition.

For example, a candidate image in which a specific structure, such as blood vessels which are at a depth of a specific mucous membrane, blood vessels having a specific thickness, and a duct, or the like is enhanced is obtained with illumination light including specific narrowband light. Enhancement in the candidate image includes not only enhancement for human vision but also enhancement for a case where a computer performs CAD or the like. Therefore, a candidate image enhanced such that a good analysis process result is obtained in a case of using CAD or the like is preferable. A plurality of types of generated candidate images are sent to the first analysis processing unit 72. As shown in FIG. 20, for example, three types of candidate images including the first candidate image, the second candidate image, and the fifth candidate image are acquired. In FIG. 20 or the like, each process written in a right field is described in a left field by "candidate image acquisition:" or the like.

The first analysis processing unit 72 performs a first analysis process on one or a plurality of types of candidate images set in advance among the plurality of types of candidate images. The number of types of candidate images on which the first analysis process is performed is set to any number. In a case where k types of candidate images are acquired, the number of types of candidate images on which the first analysis process is performed is any one of 1 to k. Herein, k is an integer of 2 or more. Also the type of candidate image on which the first analysis process is performed can be set in advance.

A first analysis process result obtained through the first analysis process is used in order to select, from a plurality of types of candidate images, at least one type of candidate image. The second analysis processing unit 74 performs a second analysis process on the selected candidate image. At least one type of candidate image selected as a target on which the second analysis process is performed by the second analysis processing unit 74 is an optimum image. A second analysis result is obtained as the second analysis processing unit 74 performs the second analysis process on the optimum image. Since a user is notified of the second analysis process result as final diagnosis support information or the like, it is preferable that an optimum image with which a good result is obtained through the second analysis process can be selected as the first analysis process result. The first analysis process result is preferably diagnosis support information. The diagnosis support information based on the first analysis process result is first diagnosis support information. One or a plurality of pieces of first diagnosis support information are obtained corresponding to the number of candidate images on which the first analysis process is performed.

The first analysis process result is information based on a candidate image, and examples thereof include a subject name such as a mucous membrane included in an observation target, a part name, a disease name, a specific structure name, and an object name that is not derived from a living body such as a treatment tool, in addition to a distance between the distal end part 12*d* of the endoscope 12 and an observation target or information obtained from a candidate image such as the brightness of the entire or specific region of the candidate image. In addition, regarding a lesion or a disease, presence or absence, an index value, a position or a region, a boundary line with a normal region, a probability, a degree of progression, or severity can be used. In addition, a specific state such as a pathological state, bleeding, or a treatment scar in an observation target shown in a candidate image can be used. The part name is preferably a characteristic part shown in a candidate image, and examples thereof include an esophageal portion, a cardiac portion, a gastrointestinal portion, a gastric body portion, a pyloric portion, a gastric horn portion, and a duodenal bulb in a case of the upper gastrointestinal tract and a cecum, a circumflex part, an ascending colon, a transverse colon, a descending colon, a sigmoid colon, and a rectum in a case of a large intestine. The specific structure includes blood vessels, ducts, pars tuberalis such as a polyp and a cancer, and concavities, and the object that is not derived from a living body includes biopsy forceps attachable to an endoscope, a treatment tool such as a snare and a foreign body extraction device, and an abdominal cavity treatment tool used in laparoscopic surgery. The lesion or disease name includes a lesion or a disease found in endoscopy of the upper gastrointestinal tract or the large intestine, and examples thereof include inflammation, redness, bleeding, a ulcer, and a polyp, gastric inflammation, Barrett's esophagus, a cancer, and ulcerative colitis. The value of the biological information is a value of biological information of an observation target, and examples thereof include oxygen saturation, a vascular density, and a value of fluorescence caused by a coloring agent.

In addition, the first diagnosis support information may be determination or identification results. Determination or identification may be identification of a tumor, a non-tumor, or the like, the stage or severity of various types of diseases, and various types of scores, such as a Mayo score and a Geboes score.

The Mayo score is a score indicating the endoscopic severity of ulcerative colitis, and based on the findings of an affected portion in the large intestine using an endoscope, it is determined to be any one of a mild stage of grades 0 and 1, a moderate stage of grade 2, or a severe stage of grade 3 depending on the presence or absence, a degree, or the like of a characteristic of a disease. For example, grade 0 is expressed as Mayo 0. Therefore, diagnosis support information is any one of Mayo 0 to Mayo 3.

In addition, the Geboes score is a score indicating the pathological severity of ulcerative colitis, and based on the findings of a biopsy tissue using a microscope, it is determined to be any one of a mild stage of Geboes 0, a pathological remission of Geboes 0 to Geboes 2A, or a pathological non-remission of Geboes 2B to Geboes 5 depending on the presence or absence, a degree, or the like of a characteristic of a disease. Therefore, the diagnosis support information is any one of Geboes 0 to Geboes 5 or Geboes 2A or Geboes 2B.

In addition, for example, a stage in a gastric cancer is classified into stages I to IV by comprehensively determining the depth of a tumor and a state of metastasis through lesion observation, a biopsy, or the like. Therefore, diagnosis support information is any one of stage I to stage IV.

In addition, a first analysis process result includes imaging conditions obtained from a candidate image, such as an electronic zoom factor. In addition, in some cases, the first analysis process result may be information from an information management server such as a hospital information system (HIS) enabled by communication and a radiology information system (RIS) or an image server such as a picture archiving and communication system for medical application (PACS). In addition, the accuracy or the like of the first analysis process result itself obtained through the image analysis process is also included.

The first analysis processing unit 72 may perform the first analysis process on a plurality of types of candidate images through the same method, but may perform the first analysis process through methods different from each other for each of the plurality of types of candidate images. That is because the type of first analysis process result from which a good result can be obtained through an image analysis process is different in some cases depending on the type of candidate image. By performing the first analysis process for each type of candidate image, an image analysis process suitable for a candidate image can be performed, and finally an optimum image with which diagnosis support information is obtained with higher accuracy can be selected, which is preferable. It is preferable that the first analysis process performed for each type of candidate image is independently performed in parallel.

Figure 21:
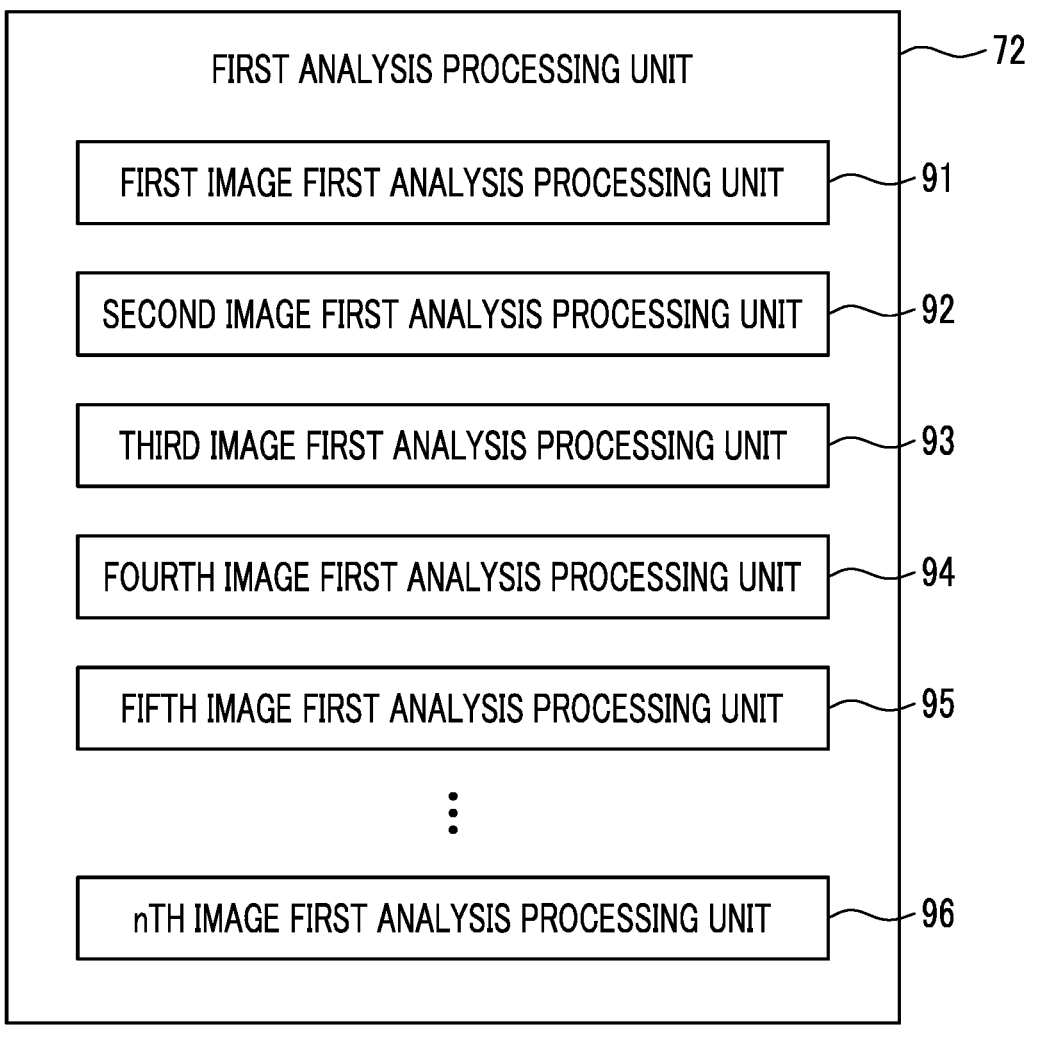
FIG. 21 is a block diagram showing a function of an image recognition unit.

In this case, as shown in FIG. 21, the first analysis processing unit 72 comprises each of first analysis processing units provided for each type of candidate image, including a first image first analysis processing unit 91, a second image first analysis processing unit 92, a third image first analysis processing unit 93, a fourth image first analysis processing unit 94, a fifth image first analysis processing unit 95, and an nth image first analysis processing unit 96. n is an integer of 6 or more, and the same number of first analysis processing units for respective images as the number of types of candidate images are included. The first image first analysis processing unit 91 performs the first analysis process on a first candidate image. Similarly, the second image first analysis processing unit 92 performs the first analysis process on a second candidate image, the third image first analysis processing unit 93 performs the first analysis process on a third candidate image, the fourth image first analysis processing unit 94 performs the first analysis process on a fourth candidate image, the fifth image first analysis processing unit 95 performs the first analysis process on a fifth candidate image, and the nth image first analysis processing unit 96 performs the first analysis process on an nth candidate image. For example, in a case where a target on which the first analysis process is performed in advance is set to three types including, the first candidate image, the second candidate image, and the fifth candidate image, that is, a case where three types of candidate images including the first candidate image, the second candidate image, and the fifth candidate image are acquired, each of three first analysis processing units including the first image first analysis processing unit 91, the second image first analysis processing unit 92, and the fifth image first analysis processing unit 95 performs the first analysis process.

In a case of performing the first analysis process on a plurality of types of candidate images through the same method, each first analysis processing unit may perform an analysis process for each of different types of candidate images. That is, each first analysis processing unit may be used commonly to different types of candidate images.

As a method of a first analysis process, a method of obtaining first diagnosis support information as a first analysis process result can be used, and examples thereof include a method of using a value based on an image, such as a pixel value and/or brightness value of a candidate image, a method of using a value of biological information, such as oxygen saturation or vascular density calculated from an image, a method of using information such as imaging conditions included in a candidate image, and a method of using association information in which a specific state of an observation target and a candidate image obtained by imaging the observation target including the specific state are associated with each other in advance.

The specific state of an observation target can be the same as examples of first diagnosis support information. The first analysis processing unit 72 preferably comprises an association information acquisition unit (not shown) that acquires association information in which a specific state of an observation target and a candidate image obtained by imaging the observation target in the specific state are associated with each other in advance. The association information is information in which in a case where a specific state of an observation target is determined in advance, a candidate image obtained by imaging the observation target, information, such as the specific state of the observation target and a region in the specific state, and the like are associated with each other. It is preferable for the first analysis processing unit 72 or each first analysis processing unit to perform the first analysis process on a newly acquired candidate image based on the association information.

Figure 22:
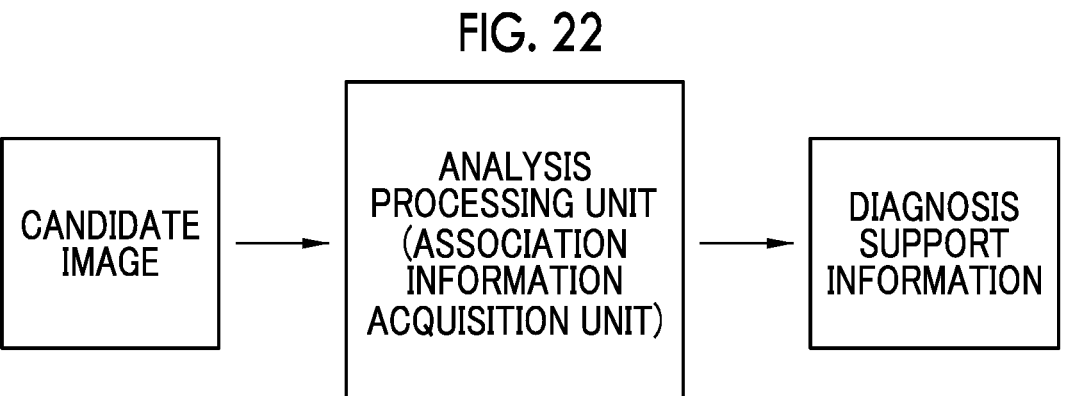
FIG. 22 is a block diagram showing a function of a first analysis processing unit.

As shown in FIG. 22, by inputting a newly acquired candidate image of which a specific state is unknown into the association information acquisition unit, the specific state of the newly acquired candidate image can be estimated and output as a first analysis process result using association information in which a candidate image included in the association information acquisition unit and a specific state of an observation target are associated with each other. In addition, the association information acquisition unit may perform learning to further acquire, as association information, each newly acquired candidate image and a specific state included in a first analysis process result output through estimation.

It is preferable that association information is included in each of the first analysis processing units from the first image first analysis processing unit 91 to the nth image first analysis processing unit 96. As an association information acquisition unit associated with a specific type of specific state is included for each type of candidate image, a good result can be obtained through an image recognition process on various types of candidate images.

For example, in a case where the type of candidate image is a second candidate image, which is a candidate image in which blood vessels are enhanced, the first analysis process corresponding to the second candidate image works as the second image first analysis processing unit 92. The second image first analysis processing unit 92 comprises an association information acquisition unit including association information related to a specific state related to blood vessels of an observation target. The association information acquisition unit performs the first analysis process of the second candidate image based on the association information and outputs details such as a region related to a specific state of an observation target included in the second candidate image. Outputting details or the like related to the specific state also includes content "a specific state is not included".

Each association information acquisition unit is, for example, a trained model in machine learning. Since a specific state of an observation target in a newly acquired candidate image is obtained more quickly or accurately as a first analysis process result, it is preferable to perform the first analysis process using the trained model based on machine learning as the association information acquisition unit. In the present embodiment, the first analysis process for outputting the specific state of the observation target is performed using the trained model in machine learning as each association information acquisition unit. In this case, it is preferable for the trained model to use what is trained for each type of candidate image in order to obtain a good analysis process result. Therefore, for example, association information included in the first image first analysis processing unit 91 and association information included in the second image first analysis processing unit 92 are preferably trained models different from each other.

Figure 23:
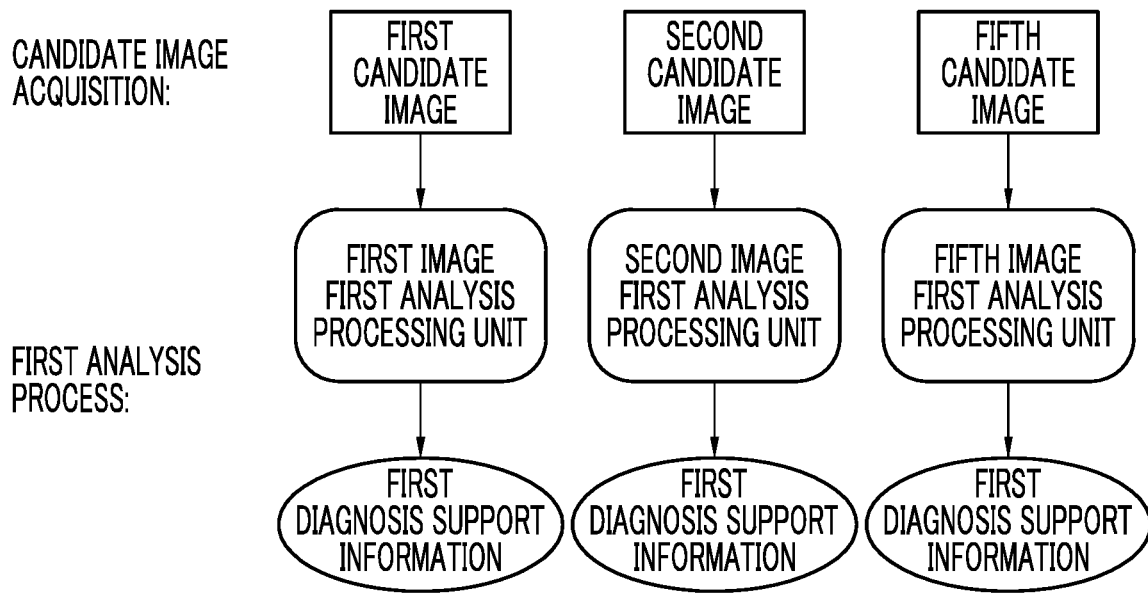
FIG. 23 is an explanatory view for describing a function of an association information acquisition unit.

As shown in FIG. 23, for example, in the three first analysis processing units including the first image first analysis processing unit 91, the second image first analysis processing unit 92, and the fifth image first analysis processing unit 95, the first analysis process of each of the first candidate image, the second candidate image, and the fifth candidate image is performed using the trained model, and first diagnosis support information is obtained by each first analysis processing unit, and in total, three pieces of first diagnosis support information are obtained.

The optimum image selection unit 73 selects, as an optimum image, at least one type of candidate image from a plurality of types of candidate images acquired by the candidate image acquisition unit 71 based on a first analysis result obtained through the first analysis process. Since the first analysis process is performed on one or the plurality of types of candidate images, one or a plurality of pieces of first diagnosis support information, which are first analysis process results, are obtained corresponding to the number of candidate images on which the first analysis process is performed. In a case where a plurality of pieces of first diagnosis support information are obtained, a total thereof is first diagnosis support information.

As a method of selecting an optimum image, various types of methods can be used. For example, an association table in which first diagnosis support information and the type of candidate image that is most preferable for the second analysis process, among a plurality of types of candidate images, are associated with each other can be prepared in advance and be used.

In a case where the light source unit 20 repeats the light emission period, it is preferable for the optimum image selection unit 73 to select at least one optimum image from a plurality of types of candidate images obtained in one light emission period. Accordingly, this is preferable since the latest optimum image is selected at all times and the latest diagnosis support information is obtained each time the light emission period is switched.

Figure 24:
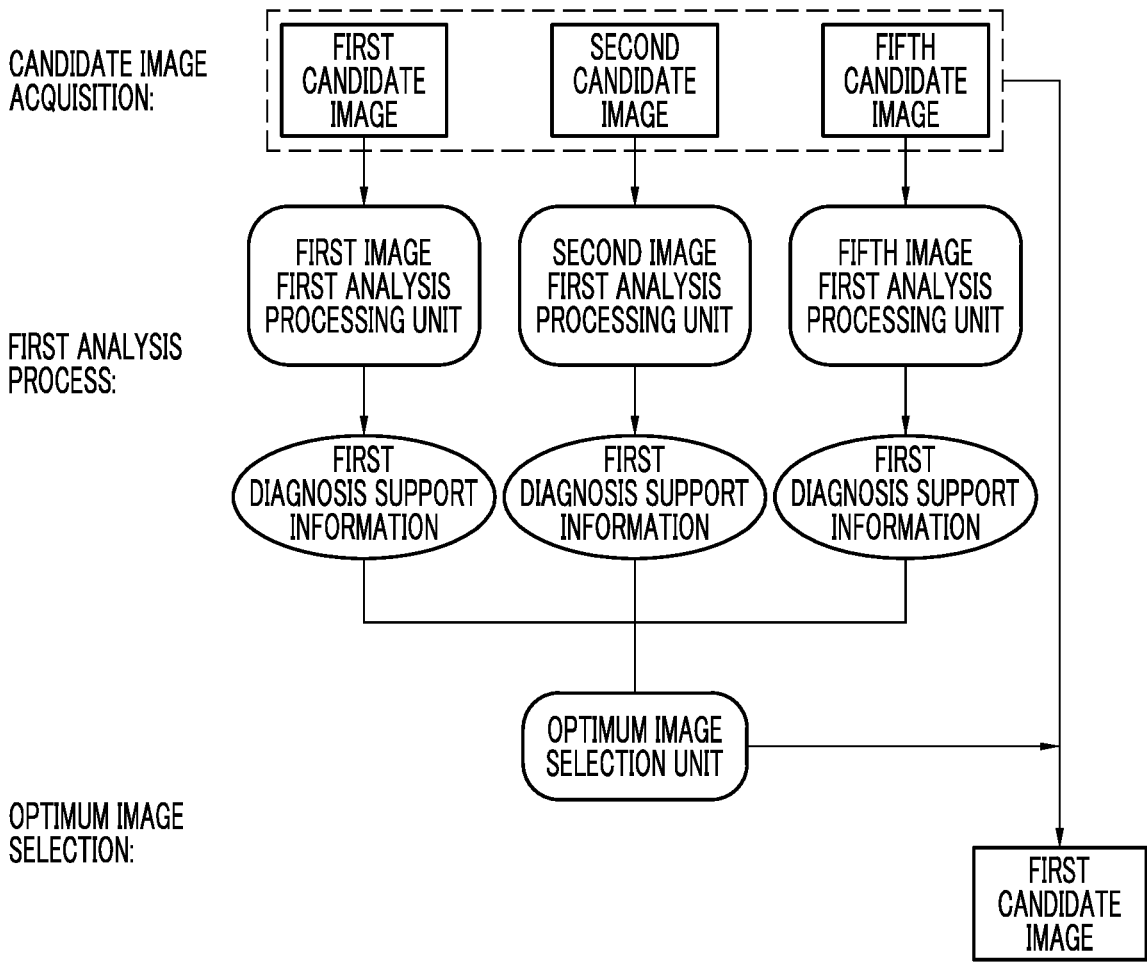
FIG. 24 is an explanatory view for describing the candidate image acquisition and a first analysis process.

As shown in FIG. 24, for example, in a case where three types of candidate images are acquired and three pieces of first diagnosis support information are obtained, the first diagnosis support information is a subject name of an observation target and a distance between the distal end part 12d of the endoscope 12 and the observation target. Specifically, in all of the three pieces of first diagnosis support information, the subject name is "mucous membrane" and the distance between the distal end part 12d of the endoscope 12 and the observation target is "distant view". The optimum image selection unit 73 integrates the three pieces of first diagnosis support information, assuming that the subject name is "mucous membrane" and the distance between the distal end part 12d of the endoscope 12 and the observation target is "distant view", and selects, as an optimum image, for example, a first candidate image, which is one type of candidate image, using the association table (not shown) included in the optimum image selection unit 73.

The second analysis processing unit 74 obtains a second analysis process result by performing the second analysis process on an optimum image. The user is notified of the second analysis process result as final diagnosis support information or the like. The second analysis process result is preferably diagnosis support information. The diagnosis support information based on the second analysis process result is second diagnosis support information. Since the second analysis process is performed on the optimum image, which is one selected candidate image, in general, one piece of second diagnosis support information is obtained.

Details of second diagnosis support information can be the same as details of first diagnosis support information. In addition, the second analysis processing unit 74 may perform the second analysis process through a method different for each type of candidate image, which is an optimum image. As in the first analysis process, that is because the type of second diagnosis support information from which a good result can be obtained through an image analysis process is different in some cases depending on the type of candidate image. This is preferable since the second diagnosis support information is obtained with higher accuracy by performing the second analysis process for each type of candidate image.

Figure 25:
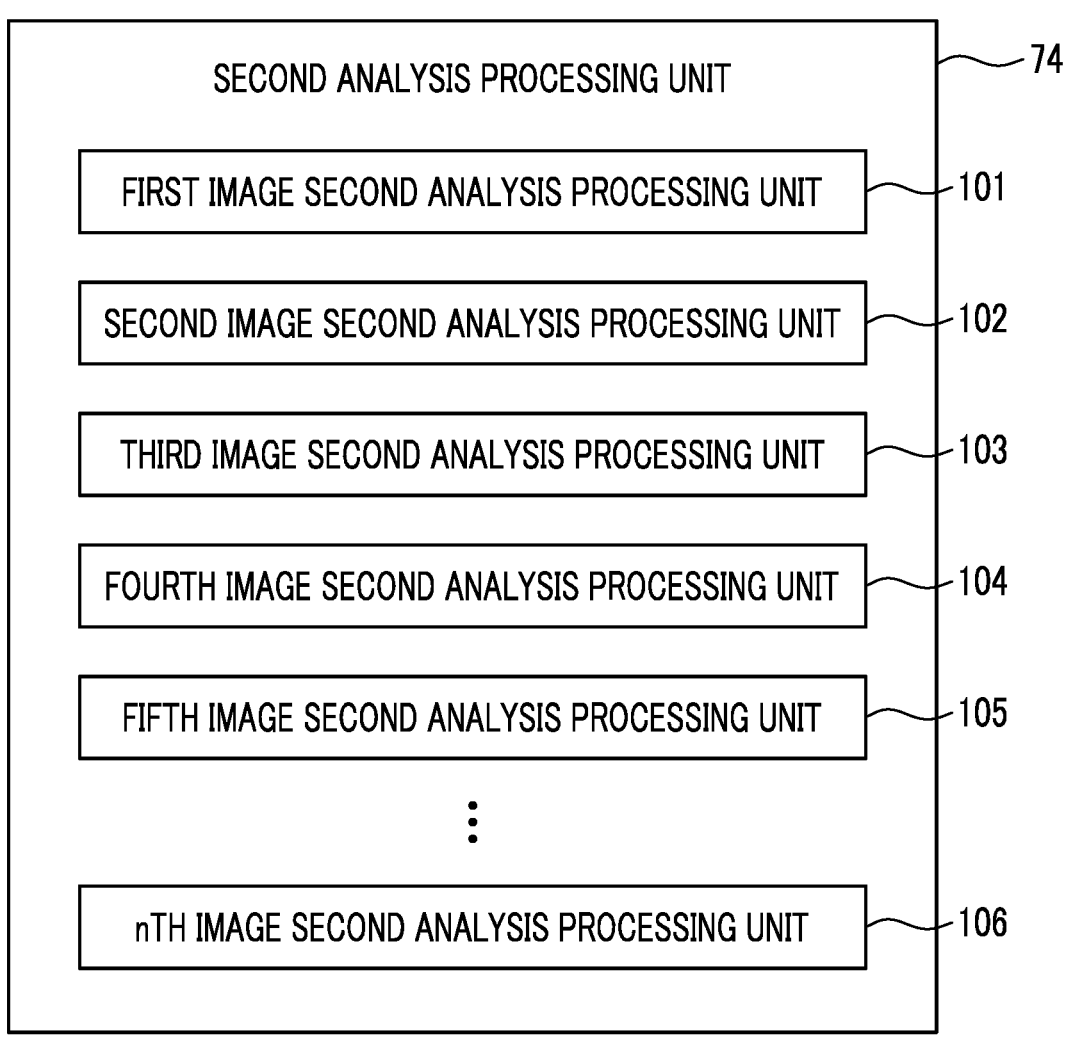
FIG. 25 is a block diagram showing a function of a second analysis processing unit.

In this case, as shown in FIG. 25, the second analysis processing unit 74 comprises a first image second analysis processing unit 101, a second image second analysis processing unit 102, a third image second analysis processing unit 103, a fourth image second analysis processing unit 104, a fifth image second analysis processing unit 105, and a nth image second analysis processing unit 106, which are provided for each type of candidate image. n is an integer of 6 or more, and the same number of second analysis processing units for respective images as the number of types of candidate images are included. The first image second analysis processing unit 101 performs the second analysis process in a case where an optimum image is a first candidate image. The same applies to the second image second analysis processing unit 102 and subsequent units.

As a method of a second analysis process, a method of obtaining second diagnosis support information as a second analysis process result can be used, and the method can be the same as the method of a first analysis process. In some cases, the first analysis processing unit 72 may serve as the second analysis processing unit 74, but in order to quickly obtain second diagnosis support information, it is preferable to perform the first analysis process and the second analysis process independently of each other. In addition, it is preferable that the first analysis process and the second analysis process are analysis processes having different contents from each other. This is because there is a possibility in which in a case of obtaining diagnosis support information having the same content by adopting an analysis process having the same content, time is needlessly wasted as the same analysis process is performed twice.

In addition, it is preferable that a second diagnosis support result is determination or an identification result, which is related to a disease. This is because a user such as a doctor is notified of the second diagnosis support result as a final diagnosis support result, and the doctor or the like performs endoscopy while diagnosing an observation target with reference to the second diagnosis support result. Examples of the second diagnosis support result preferably include an index value related to a disease, an index value related to a stage of a disease, a stage of a disease, severity of a disease, a pathological state of an observation target, and a disease location.

The second diagnosis support information is, for example, a Mayo score that is an indicator of endoscopic severity of ulcerative colitis. In this case, the second diagnosis support information is any one of Mayo scores 0 to 3. In addition, for example, the second diagnosis support information is a Geboes score that is an indicator of a pathological stage of ulcerative colitis. In this case, the second diagnosis support information is any one of Geboes 0 to Geboes 5 or Geboes 2A or Geboes 2B. In addition, for example, the second diagnosis support information is a stage of a gastric cancer. Therefore, in this case, the second diagnosis support information is any one of stages I to IV.

The severity of a disease or a degree of progression is an important determination basis in determining a treatment policy or the like. In particular, since it is important to make an accurate diagnosis at an early stage of onset for ulcerative colitis and the like, which are mainly treated medically according to the severity, it is beneficial for the endoscope system 10 or the like to accurately determine the severity through endoscopy.

In addition, it is preferable that the first analysis process and the second analysis process are performed in combination based on content set in advance. It is preferable to obtain a candidate image selected in a first analysis process result as second diagnosis support information with higher accuracy, which is a second analysis process result, in the second analysis process. Therefore, preferable content of the first analysis process and preferable content of the second analysis process can be set in advance in some cases. For example, in a case where a first analysis process result obtained through the first analysis process is a subject name of an observation target and a distance between the distal end part 12*d* of the endoscope 12 and the observation target, in a case of a short range, since there is a possibility in which a region-of-interest or the like is being observed in detail and there is a possibility of being an endoscope image showing a fine structure of a superficial layer of the mucous membrane or the like, it is preferable to adopt, as the second analysis process, a method of an analysis process of a type that obtains biological information of a disease, determination of a stage or severity, a region of a lesion portion including a normal portion and a boundary line as a second analysis process result. On the other hand, in a case of a long range, since there is a possibility in which screening of observing the entire behavior is performed and there is a possibility of being an endoscope image showing an overall state of a part, it is preferable to adopt a method of an analysis process of a type of obtaining a part name, a region of a lesion or a disease, or the like as a second analysis process result.

Figure 26:
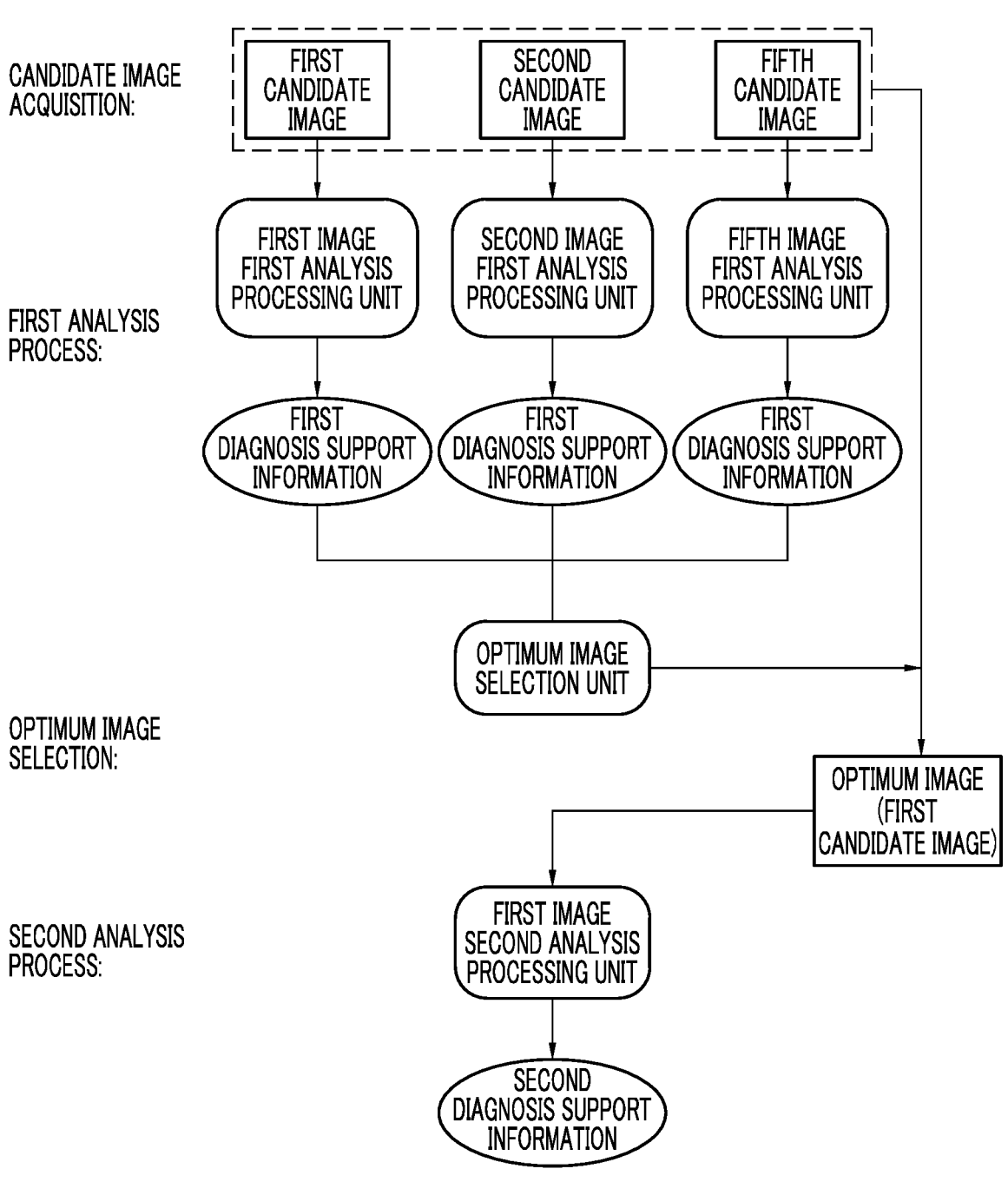
FIG. 26 is an explanatory view for describing the candidate image acquisition, the first analysis process, and optimum image selection.

In a case where a distance between the distal end part 12*d* of the endoscope 12 and an observation target is a short range, a candidate image is an endoscope image obtained through magnified observation using zoom. As shown in FIG. 26, for example, in a case where a first candidate image is selected as an optimum image, the first image second analysis processing unit 101 performs the second analysis process. As a result of the second analysis process, second diagnosis support information, which is a second analysis process result, is obtained.

Figure 27:
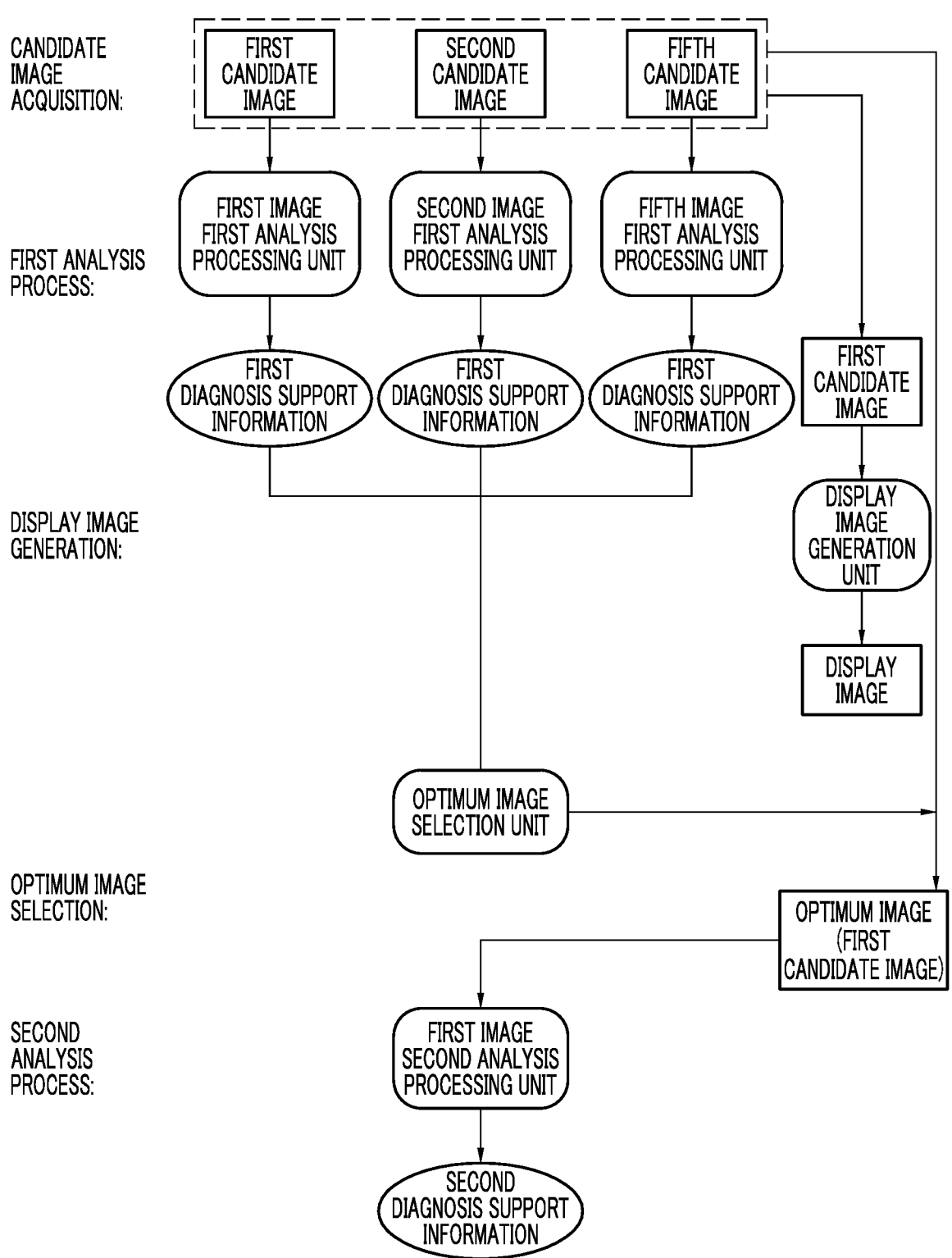
FIG. 27 is an explanatory view for describing the candidate image acquisition, the first analysis process, display image generation, the optimum image selection, and a second analysis process.

The display image generation unit 75 generates a display image to be displayed on the display 18. The display image is an endoscope image based on at least one type of candidate image among a plurality of types of candidate images, and the display image is displayed on the display 18. Which type of candidate image is to be used as a display image can be set in advance. It is preferable that a display image displayed on the display is an endoscope image having good visibility for humans since a user such as a doctor performs diagnosis or determination of an examination policy while looking at the display. For example, as shown in FIG. 27, in case where the display image is a first candidate image which is the same type as a normal observation image using white light, the display image generation unit 75 performs a necessary image process and generates a display image like the normal observation image processing unit 61. The generated display image is sent to the display control unit 57.

Figure 28:
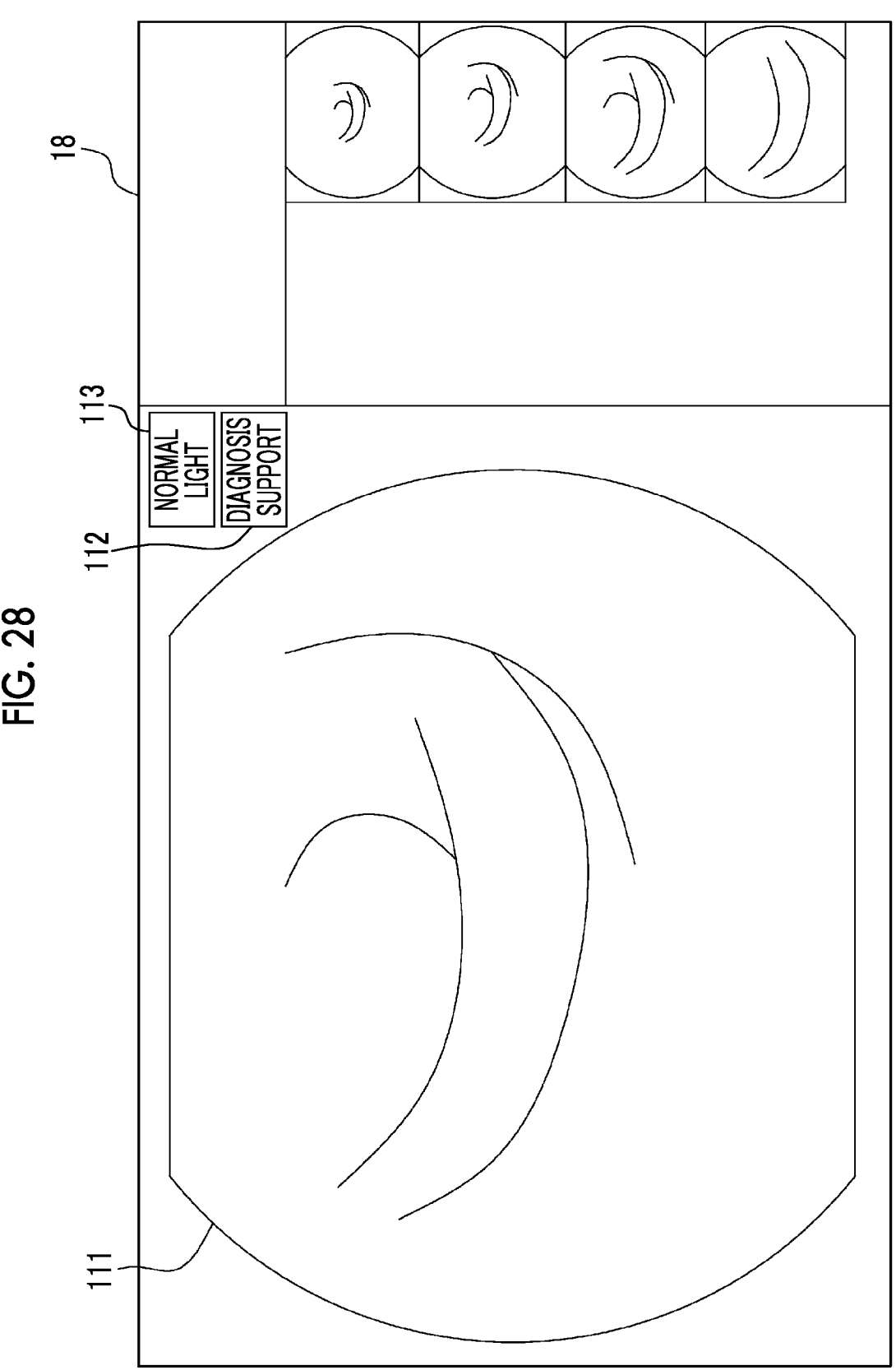
FIG. 28 is an image view showing a display on which second diagnosis support information is displayed as a text display.

The display control unit 57 displays a normal observation image on the display 18 in a case of the normal observation mode and displays a special observation image on the display 18 in a case of the special observation mode. In addition, in a case of the diagnosis support mode, control of displaying a display image on the display 18 is performed. It is preferable that the display image is continuously displayed on the display 18. Although no image is displayed as a display image in the diagnosis support mode, other acquired candidate images may be switched therebetween upon instructions and be displayed on the display 18 as a display image. As shown in FIG. 28, for example, a display image 111 is displayed on the display 18 together with a mode name display 112 for the current mode name or an endoscope image type name display 113 that indicates the type of candidate image which is a source of a display image.

By configuring as described above, the processor device 16 functioning as the image processing apparatus or the endoscope system 10 comprising the image processing apparatus determines an optimum image on which the second analysis process is to be performed using first diagnosis support information after the first diagnosis support information is obtained from a type of candidate image set in advance from a plurality of types of candidate images, and thereby time for selecting an image on which an analysis process is to be performed can be saved compared to a case where an image on which an analysis process is to be performed is selected based on information obtained therefrom without selecting an endoscope image obtained through imaging. In addition, even in a case where the number of pieces of first diagnosis support information from the first analysis process is small, since the content of the first diagnosis support information for obtaining a preferable process result in the second analysis process can be set, the accuracy of second diagnosis support information, which is finally obtained diagnosis support information, is high. Therefore, the processor device 16 functioning as the image processing apparatus or the endoscope system 10 comprising the image processing apparatus can obtain diagnosis support information based on CAD quickly or accurately. In particular, since it is important to make an accurate diagnosis at an early stage of onset for an ulcerative colitis and the like, which are mainly treated medically according to the severity, it is beneficial to accurately determine the severity, and the endoscope system 10 or the like can be preferably used.

Figure 29:
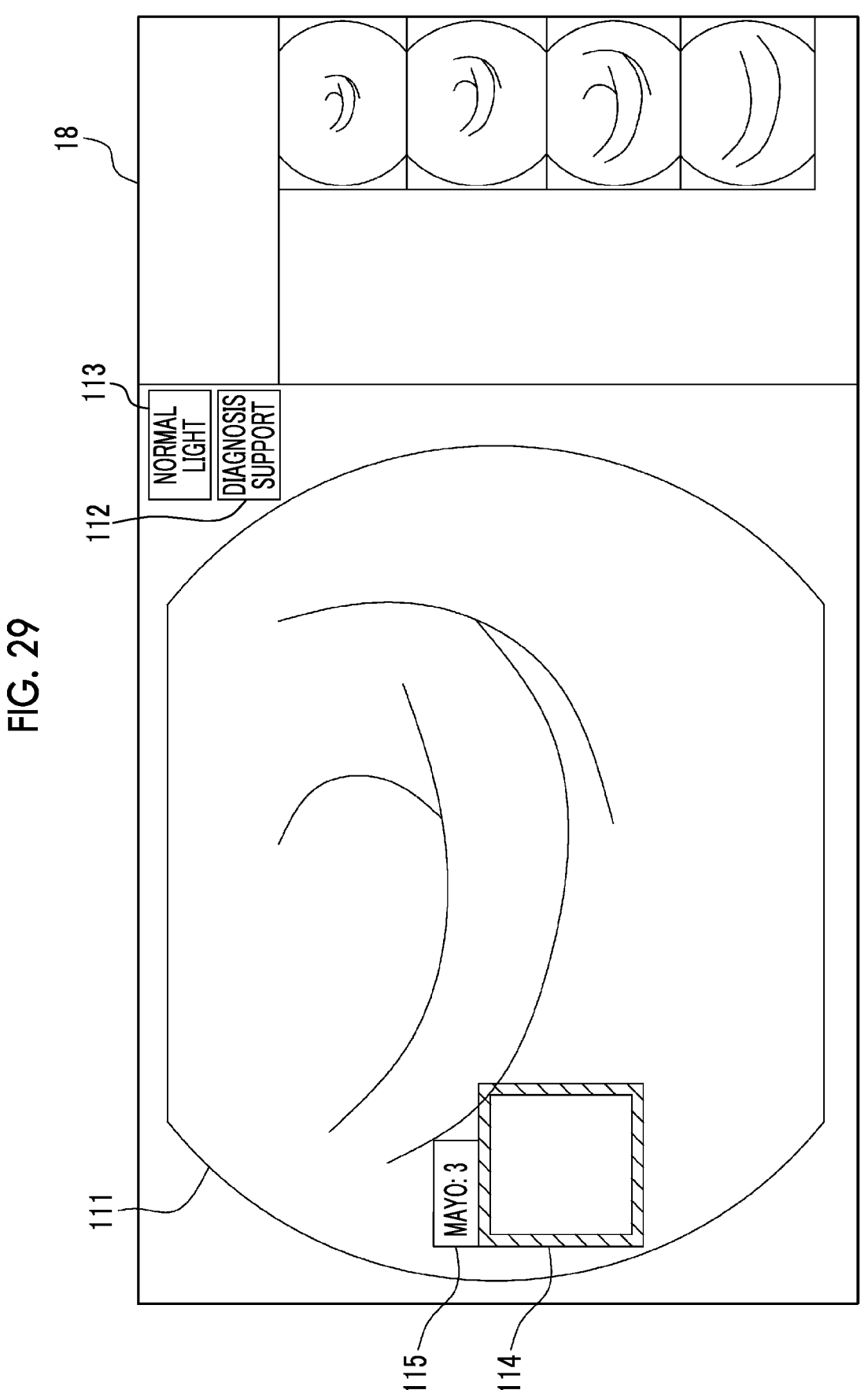
FIG. 29 is an image view showing a display on which the second diagnosis support information is displayed as a frame display and the text display.

Since it is sufficient that a user can be notified of a second analysis process result, the user may be notified through voice or the like, in addition to being displayed on the display 18, but it is preferable that the display control unit 57 performs control of displaying the second analysis process result on the display 18. It is preferable that a display form on the display 18 is a form that does not interfere with visibility of a display image for a user and that can be understood at a glance. Therefore, second diagnosis support information, which is a second analysis process result, may be displayed in a region other than the display image 111 of the display 18, or the second diagnosis support information may be displayed while being superimposed on the display image 111 by performing an image process on the display image 111. As shown in FIG. 29, for example, in a case where the second analysis process result is the second diagnosis support information and a Mayo score, a region of a lesion and a numerical value of the score may be superimposed on the display image 111 and be displayed in a colored frame display 114 and a short text display 115.

By displaying a second analysis process result on the display 18, a user can understand highly reliable diagnosis support information quickly at a glance. In addition, even in a case where a display image shows a lesion that is unlikely to be identified through diagnosis based on a normal observation image, the lesion can be prevented from being overlooked since an analysis process is performed on an optimum image suitable for the analysis process. After the second analysis process result is displayed on the display image 111, the user can make a detailed observation by quickly switching a type of display image to a type of endoscope image that allows detailed observation of the lesion shown in the second analysis process result.

In particular, in a case where the display image 111 is switched to a type of candidate image that is not displayed as the display image 111, since that type of candidate image is already obtained although not shown, the candidate image can be quickly switched to a display image.

In addition, it is preferable that the candidate image acquisition unit 71 is configured to acquire an endoscope image obtained by imaging an observation target illuminated with white illumination light emitted by the light source unit 20 as one type of candidate image. Since the endoscope image generated with white illumination light is an image that can be recognized as natural colors for humans, by using the endoscope image as a display image, a user such as a doctor can smoothly perform endoscopy.

In a case where the light source unit 20 comprises a light source processor that emits first illumination light in a first light emission pattern during a first illumination period, that emits second illumination light in a second light emission pattern during a second illumination period, and that switches between the first illumination light and the second illumination light and an image pick-up sensor that outputs a first endoscope image obtained by imaging an observation target illuminated with the first illumination light and a second endoscope image obtained by imaging the observation target illuminated with the second illumination light, it is preferable for the candidate image acquisition unit 71 to acquire the first endoscope image and the second endoscope image as candidate images. Accordingly, this is preferable since a plurality of types of candidate images can be obtained with various types of illumination light by combining the first light emission pattern and the second light emission pattern.

Figure 30:
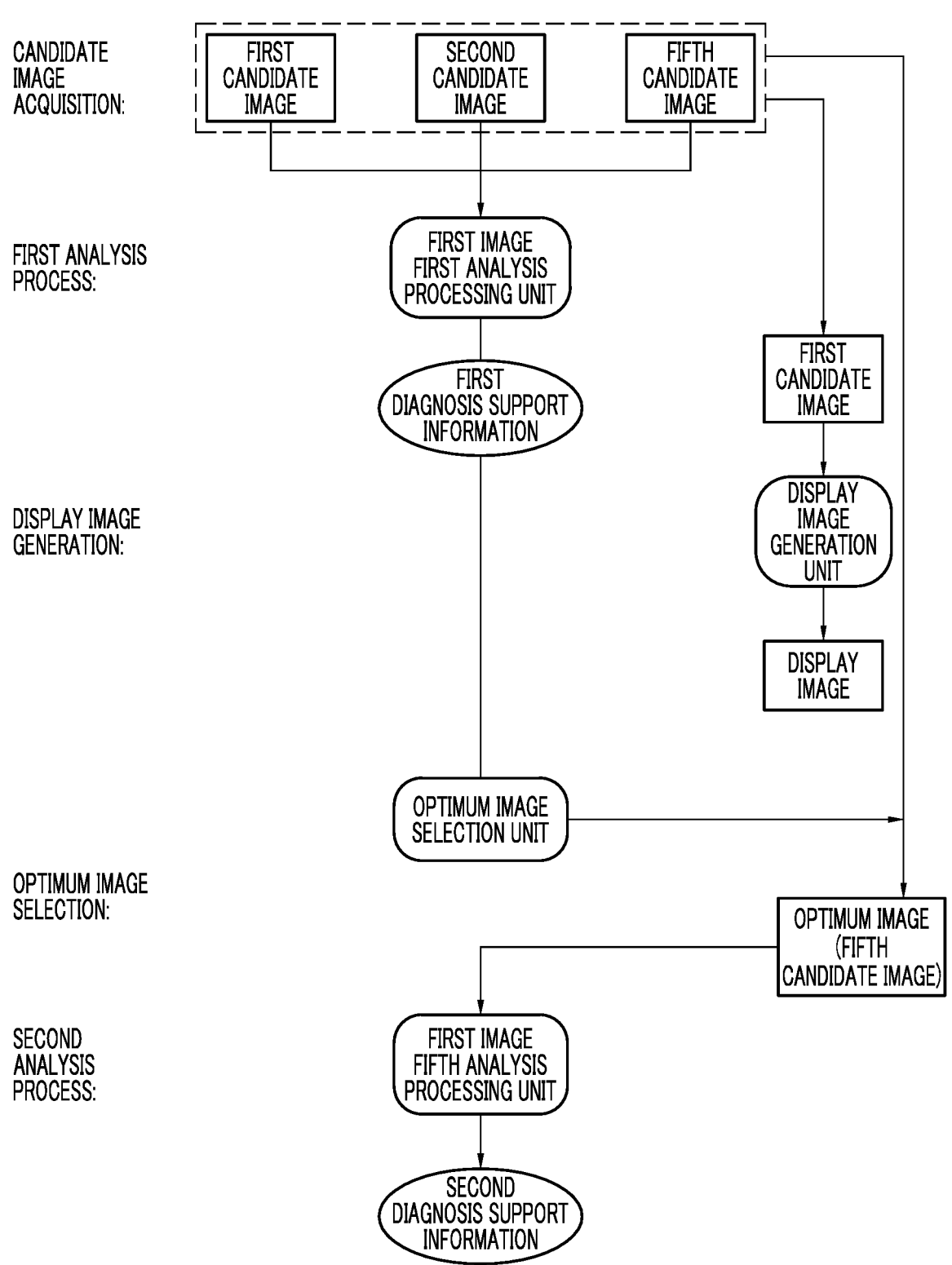
FIG. 30 is an explanatory view of selecting a fifth candidate image as an optimum image.

The first analysis processing unit 72 may perform the first analysis process on one type of candidate image set in advance among a plurality of types of candidate images. An embodiment of this case will be described below. As shown in FIG. 30, three types of candidate images including the first candidate image, the second candidate image, and the fifth candidate image are acquired. The first candidate image is an endoscope image that is the same as a normal display image obtained with white light, the second candidate image is an endoscope image in which blood vessels having a specific depth such as superficial blood vessels or structures are enhanced through a pseudo-color process, and the fifth candidate image is a color difference enhanced image and is an endoscope image in which a color difference between an abnormal portion and a normal portion is enhanced. The candidate images are based on an endoscope image captured in colonoscopic diagnosis of an ulcerative colitis patient.

Figure 31:
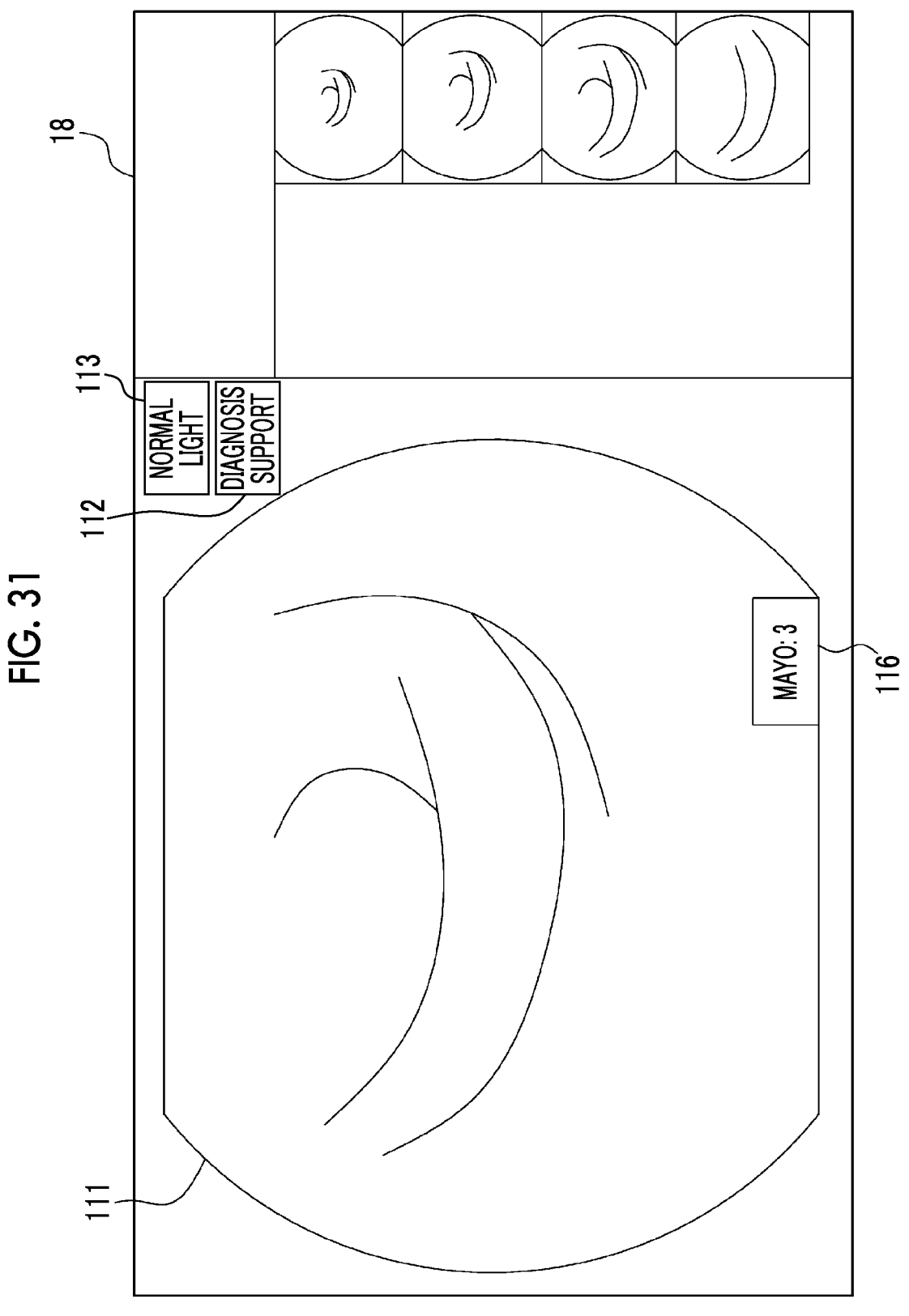
FIG. 31 is an image view showing a display on which a Mayo score is displayed.

As shown in FIG. 31, the display image generation unit 75 generates the display image 111 based on the first candidate image among the candidate images. Therefore, the display image 111 based on the first candidate image is displayed on the display 18. In addition, the first analysis processing unit 72 performs the first analysis process based on the trained model on the first candidate image which is one type of candidate image set in advance, and the first image first analysis processing unit 91 obtains a subject name of an observation target and a distance between the distal end part 12d of the endoscope 12 and the observation target as first diagnosis support information. Specifically, information, such as "mucous membrane", which is the subject name of the observation target, and "distant view", which is the distance between the distal end part 12d of the endoscope 12 and the observation target, is obtained as the first diagnosis support information.

The first diagnosis support information is sent to the optimum image selection unit 73. The optimum image selection unit 73 selects, as an optimum image, the fifth candidate image from three types of candidate images including the first candidate image, the second candidate image, and the fifth candidate image, which are acquired by the candidate image acquisition unit 71, based on a first analysis result obtained through the first analysis process. The optimum image selection unit 73 has, in advance, information that the fifth candidate image is an endoscope image on which a color difference enhancement process is performed and that is effective in diagnosis in a case where an observation condition is a distant view. The fifth candidate image selected by the optimum image selection unit 73 is sent to the second analysis processing unit 74. The second analysis processing unit 74 performs the second analysis process based on the selected fifth candidate image and obtains second diagnosis support information as a second analysis process result. Specifically, the second analysis processing unit 74 uses the trained model based on machine learning for the fifth candidate image to calculate that a Mayo score, which is an indicator of endoscopic severity for ulcerative colitis, is "3" from a state of a mucous membrane and uses the score as second diagnosis support information.

The display control unit 57 performs control of continuously displaying the display image 111 based on a first candidate image on the display 18, but performs an image process of the display image 111 such that second diagnosis support information, which is a second analysis process result, is superimposed on the display image 111 as the second analysis processing unit 74 obtains the second analysis process result. Specifically, since the second diagnosis support information is "Mayo score: 3", and the second diagnosis support information is displayed as a diagnosis support information display 116 of "Mayo: 3" in a lower right portion of the display image 111.

Figure 32:
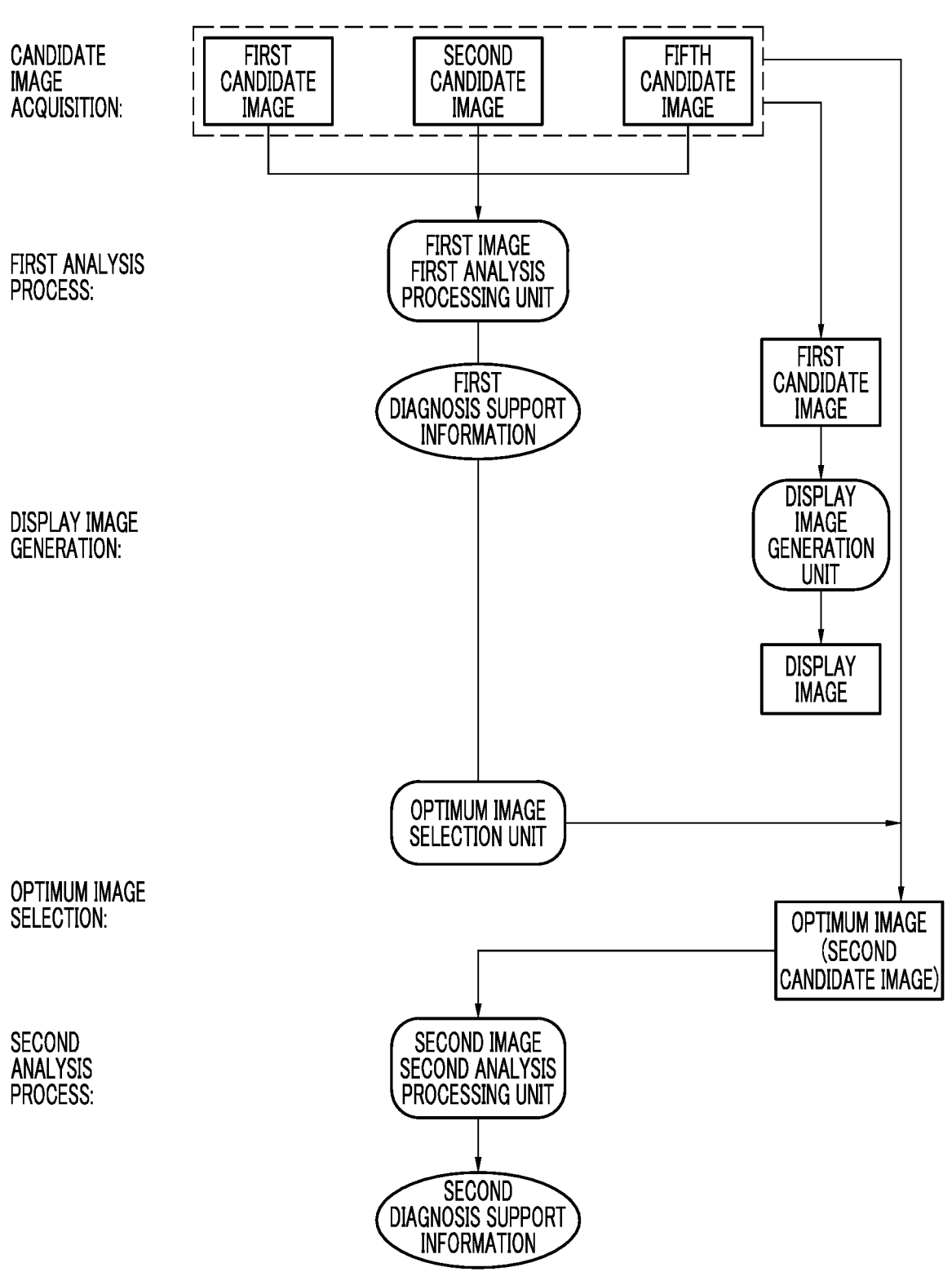
FIG. 32 is an explanatory view of selecting a second candidate image as the optimum image.

In addition, another embodiment of this case will be described below. As shown in FIG. 32, three types of candidate images including the first candidate image, the second candidate image, and the fifth candidate image are acquired. The first candidate image, the second candidate image, and the fifth candidate image are the same as described above. The candidate images are based on an endoscope image captured in colonoscopic diagnosis of an ulcerative colitis patient.

Figure 33:
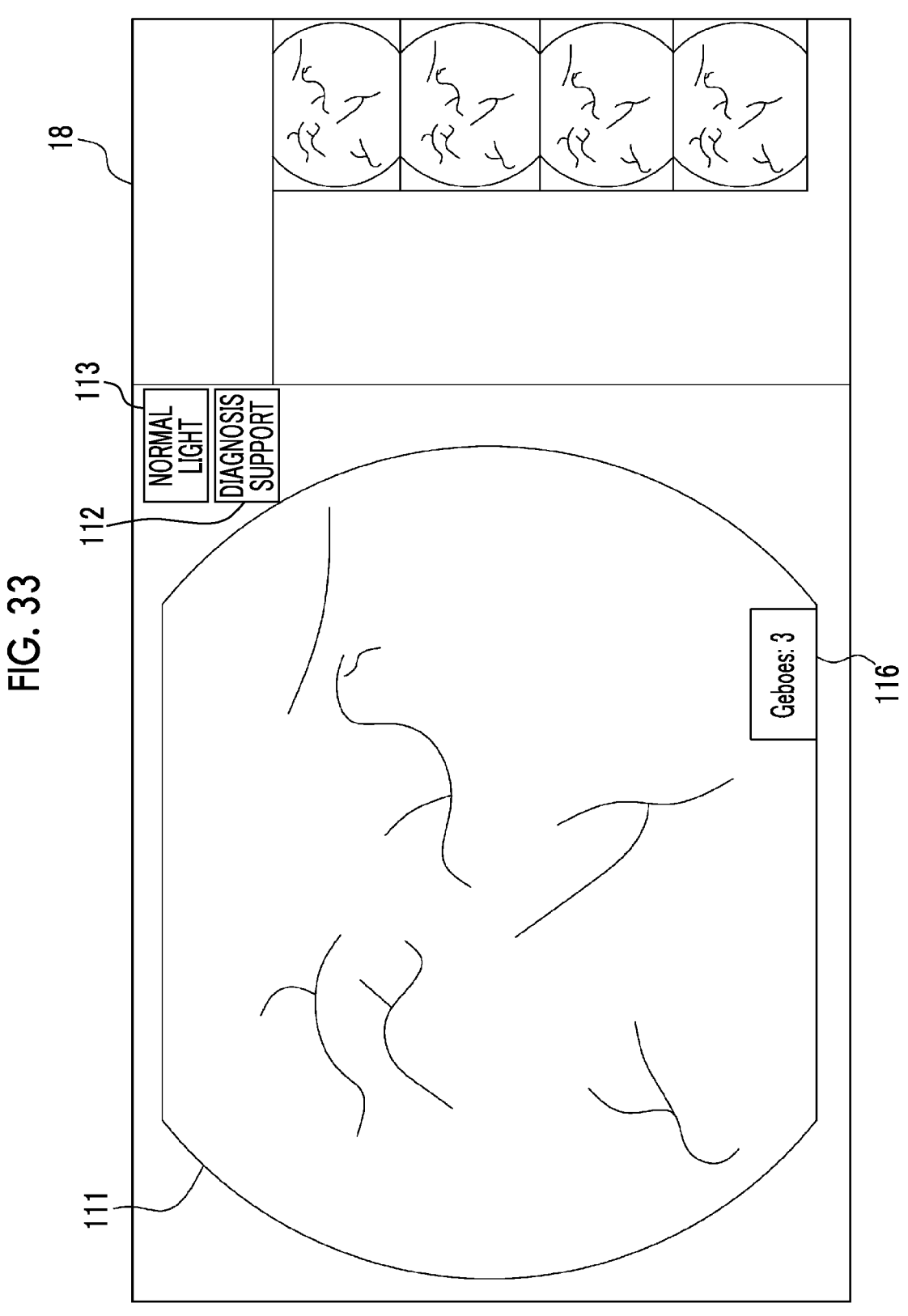
FIG. 33 is an image view showing a display on which a Geboes score is displayed.

As shown in FIG. 33, among the candidate images, the display image generation unit 75 generates the display image 111 based on a first candidate image. Therefore, the display image 111 based on the first candidate image is displayed on the display 18. In addition, the first analysis processing unit 72 performs the first analysis process based on the trained model on the first candidate image which is one type of candidate image set in advance, and the first image first analysis processing unit 91 obtains a subject name of an observation target and a distance between the distal end part 12d of the endoscope 12 and the observation target as first diagnosis support information. Specifically, information, such as "mucous membrane", which is the subject name of the observation target, and "near view", which is the distance between the distal end part 12d of the endoscope 12 and the observation target, is obtained as the first diagnosis support information.

The first diagnosis support information is sent to the optimum image selection unit 73. The optimum image selection unit 73 selects, as an optimum image, the second candidate image from three types of candidate images including the first candidate image, the second candidate image, and the fifth candidate image, which are acquired by the candidate image acquisition unit 71, based on a first analysis result obtained through the first analysis process. The optimum image selection unit 73 has, in advance, information that the second candidate image is an endoscope image on which a pseudo-color process is performed and in which blood vessels, such as superficial blood vessels, or structures are enhanced and that is effective in diagnosis in a case where an observation condition is a near view. The second candidate image selected by the optimum image selection unit 73 is sent to the second analysis processing unit 74. The second analysis processing unit 74 performs the second analysis process based on the selected second candidate image and obtains second diagnosis support information as a second analysis process result. Specifically, the second analysis processing unit 74 uses the trained model based on machine learning for the second candidate image to calculate that a Geboes score, which is an indicator of a pathological stage for ulcerative colitis, is "3" from a state of a mucous membrane and uses the score as second diagnosis support information.

The display control unit 57 performs control of continuously displaying the display image 111 based on a first candidate image on the display 18, but performs an image process of the display image 111 such that second diagnosis support information, which is a second analysis process result, is superimposed on the display image 111 as the second analysis processing unit 74 obtains the second analysis process result. Specifically, since the second diagnosis support information is "Geboes score: 3", and the second diagnosis support information is displayed as the diagnosis support information display 116 of "Geboes: 3" in the lower right portion of the display image 111.

As described above, since it is particularly important to make an accurate diagnosis at an early stage of onset for an ulcerative colitis and the like, which are mainly treated medically according to the severity, in endoscopy with the endoscope system 10 or the like, the severity can be automatically, quickly, and accurately determined.

Figure 34:
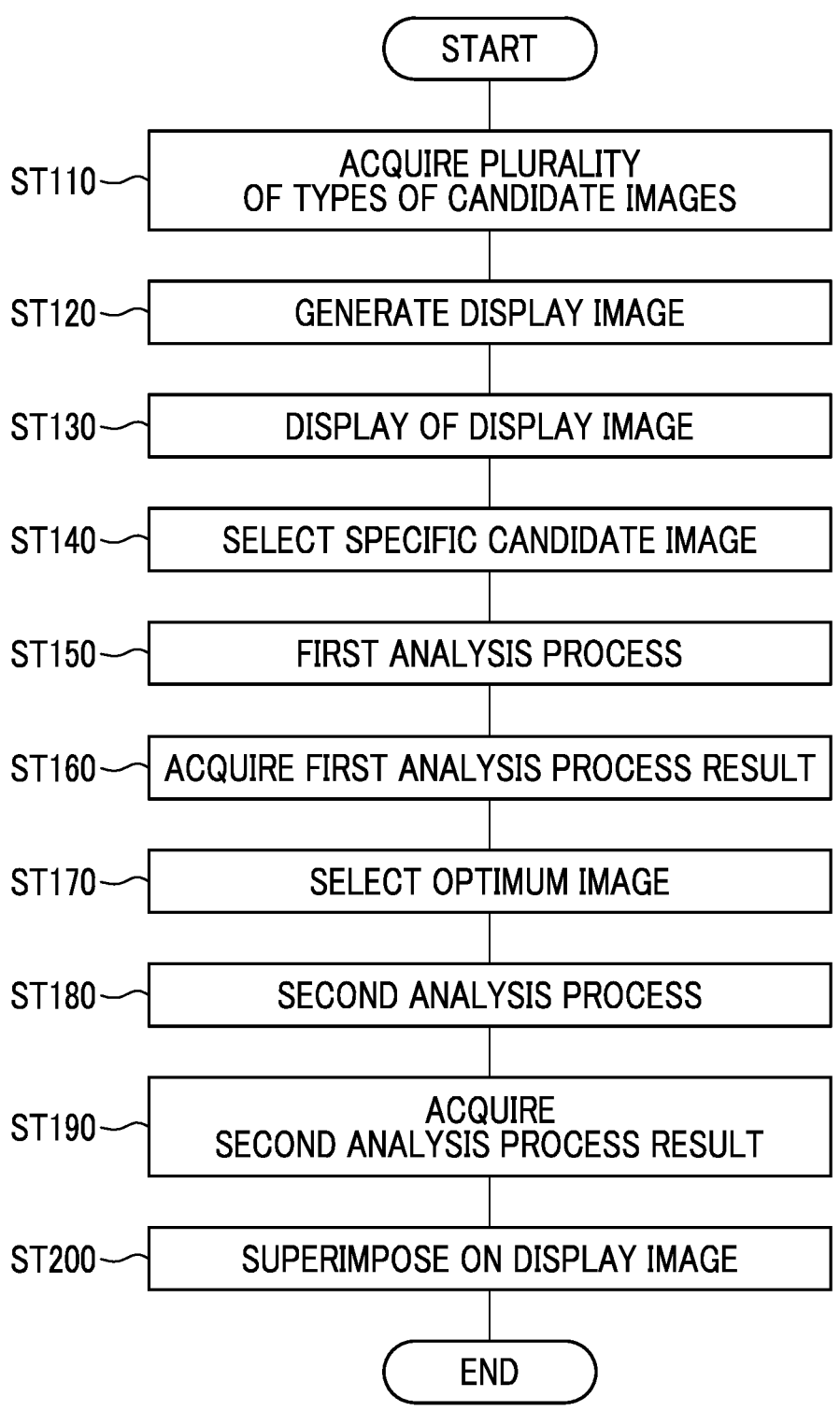
FIG. 34 is a flowchart showing the series of flows of a diagnosis support mode.

Next, the series of flows of processes for display of diagnosis support information performed by the processor device 16, which is an image analysis processing apparatus, or the endoscope system 10 will be described with reference to a flowchart shown in FIG. 34. The candidate image acquisition unit 71 acquires a plurality of types of candidate images (Step ST110). The display image generation unit 75 generates a display image based on at least one type of candidate image among the plurality of types of candidate images (Step ST120). The display control unit 57 performs control of displaying the display image on the display 18 (Step ST130).

In order for the first analysis processing unit 72 to perform the first analysis process, a type of candidate image set in advance is selected (Step ST140). The first analysis process is performed on the selected candidate image (Step ST150). A first analysis process result is obtained through the first analysis process (Step ST160). The optimum image selection unit 73 selects at least one type of optimum image from the plurality of types of candidate images based on the first analysis process result (Step ST170). The second analysis processing unit 74 performs the second analysis process on the selected optimum image (Step ST180). A second analysis process result is obtained through the second analysis process (Step ST190). The display control unit 57 performs control of superimposing the second analysis process result on the display image and displaying the superimposed display image on the display 18 (Step ST200).

Step ST120 in which the display image generation unit 75 generates a display image and Step ST130 in which the display control unit 57 performs control of displaying the display image on the display may be performed in parallel with Step ST140 in which a type of candidate image set in advance is selected in order to perform the first analysis process.

Figure 35:
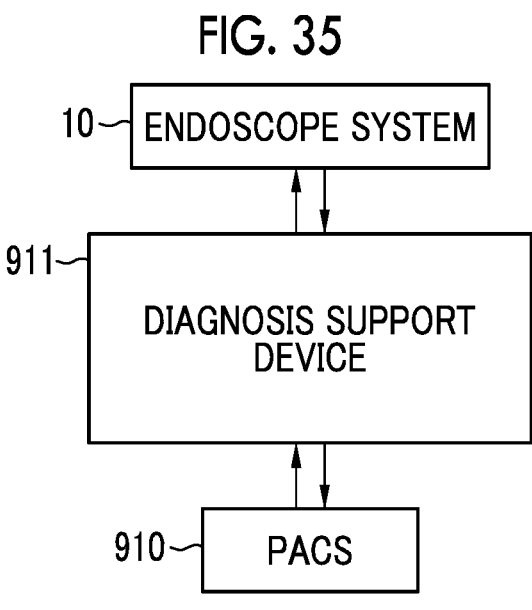
FIG. 35 is an explanatory view showing a diagnosis support device.
Figure 36:
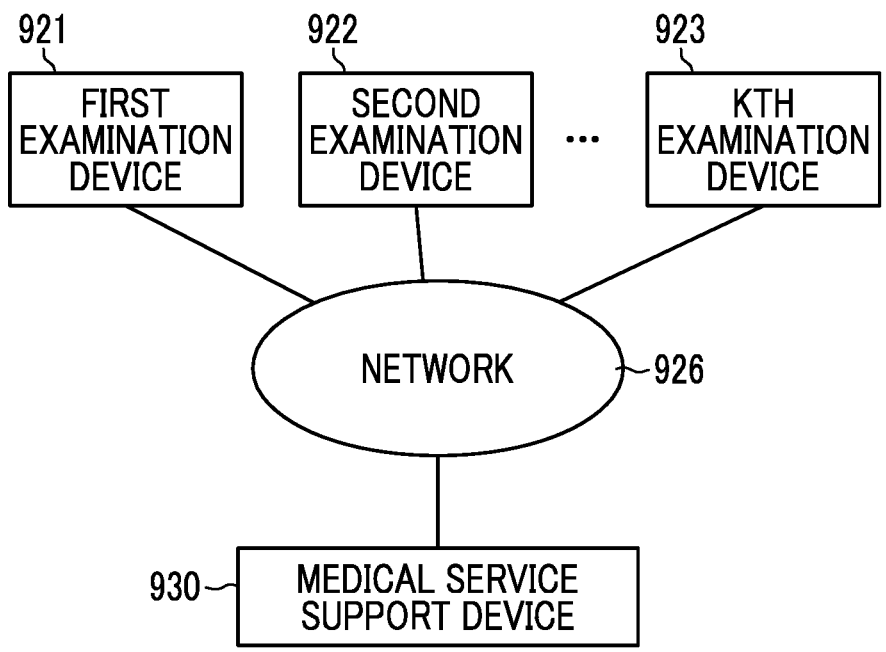
FIG. 36 is an explanatory view showing a medical service support device.

Although the processor device 16 functions as the image processing apparatus in the embodiment, a modification example, and the like, the image processing apparatus including the image processing unit 56 may be provided separately from the processor device 16. In addition, as shown in FIG. 35, the image processing unit 56 can be provided at a diagnosis support device 911 that acquires an RAW image captured by the endoscope 12, for example, directly from the endoscope system 10 or indirectly from picture archiving and communication systems (PACS) 910. In addition, as shown in FIG. 36, the image processing unit 56 can be provided at a medical service support device 930 that is connected to various types of examination devices including a first examination device 921, a second examination device 922, . . . , and a Kth examination device 923, including the endoscope system 10, via a network 926.

Each of the embodiments and the modification examples can be performed in any combination of some or all of the embodiments and the modification examples. In addition, although the endoscope 12 uses a so-called soft endoscope having the flexible insertion part 12*a* in each of the embodiments and the modification examples, the present invention is suitable also in a case of using a capsule-type endoscope used by swallowing an observation target or a hard endoscope (laparoscope) using a surgical operation or the like.

The embodiments, the modification examples, and the like include a program for an image processing apparatus causing a computer to realize a candidate image acquisition function of acquiring a plurality of types of candidate images based on an endoscope image obtained by imaging an observation target using an endoscope, a display control function of performing control of displaying, on a display, a display image based on at least one type of candidate image among the plurality of types of candidate images, a first analysis processing function of performing a first analysis process on one or the plurality of types of candidate images set in advance among the plurality of types of candidate images, an optimum image selection function of selecting at least one type of candidate image from the plurality of types of candidate images as an optimum image based on a first analysis process result obtained through the first analysis process, and a second analysis processing function of obtaining diagnosis support information by performing a second analysis process on the optimum image.

In the embodiment, hardware structures of processing units that perform various types of processes, such as the image processor and the light source processor 22, including the central control unit 51, the image acquisition unit 52, the image processing unit 56, and the display control unit 57 included in the processor device 16, which is the image processing apparatus, are various types of processors shown below. The various types of processors include a central processing unit (CPU) that is a general-purpose processor functioning as various types of processing units, which execute software (program) and function as various types of processing units, a programmable logic device (PLD) that is a processor which can change a circuit configuration after manufacturing, such as a field programmable gate array (FPGA), and a dedicated electric circuit that is a processor which has a circuit configuration exclusively designed for executing various types of processes.

One processing unit may be composed of one of the various types of processors, or may be composed of the same type or different types of two or more processors (for example, a plurality of FPGAs or a combination of a CPU and an FPGA). In addition, one processor may configure a plurality of processing units. As an example of configuring a plurality of processing units with one processor, first, there is a form in which one processor is configured by a combination of one or more CPUs and software and the processor functions as the plurality of processing units, as represented by a computer such as a client and a server. Second, there is a form in which a processor that realizes functions of the entire system including the plurality of processing units with one integrated circuit (IC) chip is used, as represented by a system on chip (SoC). As described above, the various types of processing units are composed of one or more of the various types of processors used as a hardware structure.

Further, the hardware structures of the various types of processors are, more specifically, an electric circuit (circuitry) in a form in which circuit elements such as semiconductor elements are combined.

The present invention can be useful also in a system, a device, or the like that acquires a medical image (including a video image) other than an endoscope image, in addition to an endoscope system that acquires an endoscope image or the like, a processor device, other related devices, and the like. For example, the present invention can be applied to an ultrasonic examination device, an X-ray image imaging device (including a computed tomography (CT) examination device and a mammography device), a magnetic resonance imaging (MRI) device, and the like.

EXPLANATION OF REFERENCES

10: endoscope system
12: endoscope
12*a*: insertion part
12*b*: operating part
12*c*: bendable part
12*d*: distal end part
12*e*: angle knob
12*f*: scope button No. 1
12*g*: scope button No. 2
12*h*: zoom operation part
14: light source device
16: processor device

18: display
19: keyboard
20: light source unit
20*a*: V-LED
20*b*: B-LED
20*c*: G-LED
20*d*: R-LED
22: light source processor
30*a*: illumination optical system
30*b*: imaging optical system
41: light guide
42: illumination lens
43: objective lens
44: zoom lens
45: image sensor
46: imaging processor
51: central control unit
52: image acquisition unit
53: DSP
54: noise-reduction unit
55: conversion unit
56: image processing unit
57: display control unit
61: normal observation image processing unit
62: special observation image processing unit
63: diagnosis support image processing unit
71: candidate image acquisition unit
72: first analysis processing unit
73: optimum image selection unit
74: second analysis processing unit
75: display image generation unit
81: first candidate image generation unit
82: second candidate image generation unit
83: third candidate image generation unit
84: fourth candidate image generation unit
84*a*: oxygen saturation signal ratio calculation unit
84*b*: oxygen saturation calculation table
84*c*: oxygen saturation calculation unit
84*d*: oxygen saturation image generation unit
85: fifth candidate image generation unit
85*a*: color difference extension signal ratio calculation unit
85*b*: color difference extension processing unit
85*c*: color difference extension image generation unit
86: nth candidate image generation unit
91: first image first analysis processing unit
92: second image first analysis processing unit
93: third image first analysis processing unit
94: fourth image first analysis processing unit
95: fifth image first analysis processing unit
96: nth image first analysis processing unit
101: first image second analysis processing unit
102: second image second analysis processing unit
103: third image second analysis processing unit
104: fourth image second analysis processing unit
105: fifth image second analysis processing unit
106: nth image second analysis processing unit
111: display image
112: mode name display
113: endoscope image type name display
114: frame display
115: text display
116: diagnosis support information display
910: PACS
911: diagnosis support device
921: first examination device
922: second examination device

923: Kth examination device
926: network
930: medical service support device
P1: first illumination period
P2: second illumination period
FL: frame
L1: first illumination light
L2*a*, L2*b*: second illumination light
Q1, Q2, Q3, Q4, Q5: light emission period
SP1, SP2, SP3, SP4: second illumination light optical spectrum
A1, A2: range
ELx, EL1, EL2, EL3, EL4, ELy: isoline of oxygen saturation
ST110 to ST200: step

What is claimed is:

1. An image processing apparatus comprising an image processor, wherein the image processor is configured to:

acquire a plurality of types of candidate images based on an endoscope image obtained by imaging an observation target using an endoscope;

perform control of displaying, on a display, a display image based on at least one type of the candidate image among the plurality of types of candidate images;

perform a first analysis process through a plurality of different candidate methods on each of the plurality of types of candidate images set in advance among the plurality of types of candidate images;

select at least one type of the candidate image from the plurality of types of candidate images as an optimum image based on a first analysis process result obtained through the first analysis process through the plurality of different candidate methods, wherein the optimum image is subject to the first analysis process through an optimum method among the plurality of different candidate methods;

and perform a second analysis process on the optimum image by using the optimum method to obtain a second analysis process result, wherein the plurality of different candidate methods are different image enhancement methods that enhance structure contrast and color contrast on the observation subject.

2. The image processing apparatus according to claim 1, wherein the image processor is configured to perform control of displaying the second analysis process result on the display.

3. The image processing apparatus according to claim 1, wherein the image processor is configured to perform control of superimposing the second analysis process result on the display image and displaying the superimposed display image.

4. The image processing apparatus according to claim 1, wherein the first analysis process and the second analysis process are analysis processes having contents different from each other.

5. The image processing apparatus according to claim 1, wherein the image processor is configured to:

generate the candidate image by performing an enhancement process on the endoscope image; and distinguish types of the candidate images depending on presence or absence or a type of the enhancement process and to acquire the plurality of types of candidate images.

6. The image processing apparatus according to claim 5, wherein the enhancement process is a color enhancement process and/or a structure enhancement process.

7. An endoscope system comprising:
the image processing apparatus according to claim 1; and
a light source unit that emits illumination light with which the observation target is irradiated.

8. The endoscope system according to claim 7, wherein the image processor is configured to acquire the endoscope image obtained by imaging the observation target illuminated with each of a plurality of types of illumination light emitted by the light source unit, which have optical spectra different from each other, as each of different types of the candidate images from each other.

9. The endoscope system according to claim 7, wherein the light source unit repeatedly emits each of a plurality of types of illumination light, which have optical spectra different from each other, in one light emission period consisting of order set in advance.

10. The endoscope system according to claim 9, wherein the image processor is configured to select at least one optimum image from the plurality of types of candidate images obtained in the one light emission period.

11. The endoscope system according to claim 7, further comprising:
a light source processor configured to emit first illumination light in a first light emission pattern during a first illumination period, emit second illumination light in a second light emission pattern during a second illumination period, and switch between the first illumination light and the second illumination light; and
an image pick-up sensor that outputs a first endoscope image obtained by imaging the observation target illuminated with the first illumination light and a second endoscope image obtained by imaging the observation target illuminated with the second illumination light,
wherein the image processor is configured to acquire the first endoscope image and the second endoscope image as the candidate images.

12. The endoscope system according to claim 7, wherein the image processor is configured to acquire the endoscope image obtained by imaging the observation target illuminated with white illumination light emitted by the light source unit as one type of the candidate image.

13. The endoscope system according to claim 7, wherein the image processor is configured to acquire the endoscope image obtained by imaging the observation target illuminated with illumination light, which is emitted by the light source unit and includes narrow-band light in a wavelength range set in advance, as one type of the candidate image.

14. An operation method of an image processing apparatus comprising:
acquiring a plurality of types of candidate images based on an endoscope image obtained by imaging an observation target using an endoscope;

performing control of displaying, on a display, a display image based on at least one type of the candidate image among the plurality of types of candidate images;
performing a first analysis process through a plurality of different candidate methods on each of the plurality of types of candidate images set in advance among the plurality of types of candidate images;
selecting at least one type of the candidate image from the plurality of types of candidate images as an optimum image based on a first analysis process result obtained through the first analysis process through the plurality of different candidate methods, wherein the optimum image is subject to the first analysis process through an optimum method among the plurality of different candidate methods;
and
performing a second analysis process on the optimum image by using the optimum method to obtain a second analysis process result,
wherein the plurality of different candidate methods are different image enhancement methods that enhance structure contrast and color contrast on the observation subject.

15. A non-transitory computer readable medium for storing a computer-executable program for causing a computer to function as an image processing apparatus, the program causing the computer to execute:
acquiring a plurality of types of candidate images based on an endoscope image obtained by imaging an observation target using an endoscope;
performing control of displaying, on a display, a display image based on at least one type of the candidate image among the plurality of types of candidate images;
performing a first analysis process through a plurality of different candidate methods on each of the plurality of types of candidate images set in advance among the plurality of types of candidate images;
selecting at least one type of the candidate image from the plurality of types of candidate images as an optimum image based on a first analysis process result obtained through the first analysis process through the plurality of different methods, wherein the optimum image is subject to the first analysis process through an optimum method among the plurality of different candidate methods;
and
performing a second analysis process on the optimum image by using the optimum method to obtain a second analysis process result,
wherein the plurality of different candidate methods are different image enhancement methods that enhance structure contrast and color contrast on the observation subject.

16. The image processing apparatus according to claim 1, wherein the plurality of types of candidate images comprise an endoscope image obtained with white light, an endoscope image in which blood vessels or structures are enhanced, and an endoscope image in which a color difference between an abnormal portion and a normal portion is enhanced.

* * * * *